( 12 ) United States Patent
Forsell

(10) Patent No.: US 10,251,754 B2
(45) Date of Patent: Apr. 9, 2019

(54) KNEE JOINT DEVICE

(76) Inventor: Peter Forsell, Bouveret (CH)

( * ) Notice: Subject to any disclaimer, the term of this patent is extended or adjusted under 35 U.S.C. 154(b) by 709 days.

(21) Appl. No.: 13/978,303

(22) PCT Filed: Jan. 4, 2012

(86) PCT No.: PCT/SE2012/050004
§ 371 (c)(1),
(2), (4) Date: Jan. 27, 2014

(87) PCT Pub. No.: WO2012/093961
PCT Pub. Date: Jul. 12, 2012

(65) Prior Publication Data
US 2014/0135926 A1 May 15, 2014

(30) Foreign Application Priority Data

Jan. 5, 2011 (SE) ...................................... 1100011
Jan. 5, 2011 (SE) ...................................... 1100012

(51) Int. Cl.
*A61F 2/38* (2006.01)
*A61F 2/08* (2006.01)
(52) U.S. Cl.
CPC .......... *A61F 2/3836* (2013.01); *A61F 2/0811* (2013.01); *A61F 2/3859* (2013.01);
(Continued)
(58) Field of Classification Search
CPC ........ A61F 2/384; A61F 2/3836; A61F 2/389; A61F 2/38; A61F 2/3854; A61F 2/0835;
(Continued)

(56) References Cited

U.S. PATENT DOCUMENTS 3,846,846 A * 11/1974 Fischer ................. A61F 2/3662
411/33
4,520,511 A * 6/1985 Gianezio ............... A61F 2/3609
606/63

(Continued)

FOREIGN PATENT DOCUMENTS

FR 08 53040 * 5/2009
GB 2403416 1/2005
WO WO 2008/000496 1/2008

OTHER PUBLICATIONS

International Search Report for PCT/SE2012/050004 dated Apr. 17, 2012.

(Continued)

*Primary Examiner* — Alvin J Stewart

(57) ABSTRACT

A medical device for creating an artificial knee joint or an artificial cruciate ligament in a mammal patient, the medical device comprising a transversal member adapted to be placed through at least three layers of cortical bone of the distal portion of the femoral bone, out of totally four cortical layers along a prolongation of the transversal member. The transversal member is adapted to be involved in the artificial knee joint or the artificial cruciate ligament, wherein the transversal member comprises at least one fixation portion adapted to be involved in fixation of the transversal member to at least one of the at least four layers of femoral cortical bone.

46 Claims, 19 Drawing Sheets

(52) U.S. Cl.
CPC .............. *A61F 2002/0829* (2013.01); *A61F 2002/0864* (2013.01); *A61F 2002/0888* (2013.01)

(58) Field of Classification Search
CPC ............ A61F 2002/0823; A61F 2/0811; A61F 2002/30484; A61F 2002/30092; A61F 2/08; A61F 2/0805
See application file for complete search history.

(56) References Cited

U.S. PATENT DOCUMENTS

| | | | | |
|---|---|---|---|---|
| 4,744,793 A * | 5/1988 | Parr | ...................... | A61F 2/0811 623/13.14 |
| 5,282,867 A * | 2/1994 | Mikhail | ................. | A61F 2/0811 623/13.12 |
| 5,702,481 A * | 12/1997 | Lin | ........................ | A61F 2/3662 424/423 |
| 5,707,395 A * | 1/1998 | Li | ....................... | A61B 17/0401 606/232 |
| 5,957,953 A * | 9/1999 | DiPoto | ............... | A61B 17/0401 606/232 |
| 6,190,411 B1 * | 2/2001 | Lo | ......................... | A61F 2/0811 623/13.13 |
| 6,554,833 B2 * | 4/2003 | Levy | .................. | A61B 17/7258 606/62 |
| 6,554,862 B2 * | 4/2003 | Hays | ..................... | A61F 2/0811 623/13.11 |
| 6,905,513 B1 * | 6/2005 | Metzger | .................... | A61F 2/08 623/20.14 |
| 7,297,165 B1 | 11/2007 | Kriek | | |
| 7,658,767 B2 | 2/2010 | Wyss | | |
| 7,771,483 B2 | 8/2010 | Justin et al. | | |
| 7,909,825 B2 * | 3/2011 | Saravia | .............. | A61B 17/1725 606/63 |
| 8,057,524 B2 * | 11/2011 | Meridew | ............... | A61F 2/0805 606/313 |
| 8,435,294 B2 * | 5/2013 | Montgomery | ..... | A61B 17/0401 623/13.14 |
| 9,155,574 B2 * | 10/2015 | Saravia | .............. | A61B 17/7208 |
| 9,486,318 B2 * | 11/2016 | Forsell | .................. | A61F 2/3603 |
| 9,770,323 B2 * | 9/2017 | Gadikota | .............. | A61F 2/0811 |
| 9,827,025 B2 * | 11/2017 | Jansen | ................ | A61B 17/7216 |
| 2002/0055780 A1 * | 5/2002 | Sklar | ...................... | A61F 2/0811 623/13.12 |
| 2003/0009220 A1 * | 1/2003 | Seyr | ...................... | A61F 2/0811 623/13.14 |
| 2004/0024469 A1 * | 2/2004 | Ferree | .................. | A61B 17/164 623/23.26 |
| 2004/0153153 A1 * | 8/2004 | Elson | ......................... | A61F 2/08 623/13.14 |
| 2005/0065533 A1 * | 3/2005 | Magen | ...................... | A61F 2/08 606/102 |
| 2006/0155287 A1 * | 7/2006 | Montgomery | ..... | A61B 17/0401 623/13.14 |
| 2007/0225805 A1 * | 9/2007 | Schmieding | .......... | A61F 2/0811 623/13.14 |
| 2008/0027430 A1 * | 1/2008 | Montgomery | ........ | A61F 2/0811 606/60 |
| 2008/0183290 A1 * | 7/2008 | Baird | .................... | A61F 2/0811 623/13.14 |
| 2008/0255671 A1 | 10/2008 | Kriek | | |
| 2009/0088862 A1 * | 4/2009 | Thomas | .............. | A61F 2/30721 623/20.36 |
| 2009/0318976 A1 * | 12/2009 | Gabriel | ................. | A61F 2/3836 606/283 |
| 2010/0222889 A1 * | 9/2010 | Howling | .................... | A61F 2/38 623/20.21 |
| 2011/0196490 A1 * | 8/2011 | Gadikota | ............. | A61B 17/686 623/13.14 |
| 2011/0295254 A1 * | 12/2011 | Brunnarius | ........ | A61B 17/7258 606/64 |
| 2015/0025631 A1 * | 1/2015 | Bouduban | ............. | A61F 2/0811 623/13.14 |
| 2016/0038274 A1 * | 2/2016 | Heaven | ................. | A61F 2/0811 623/13.12 |
| 2017/0143473 A1 * | 5/2017 | Beck, Jr. | ................ | A61F 2/0811 |
| 2017/0202660 A1 * | 7/2017 | Baird | ................... | A61F 2/0811 |
| 2018/0036114 A1 * | 2/2018 | Pilgeram | ............... | A61F 2/0805 |

OTHER PUBLICATIONS

Written Opinion of the International Searching Authority for PCT/SE2012/050004 dated Apr. 17, 2012.

Office Action for the Japanese Patent Application No. 2013-548385 (based on International Appln. No. PCT/SE2012/050004) dated Dec. 15, 2015.

\* cited by examiner

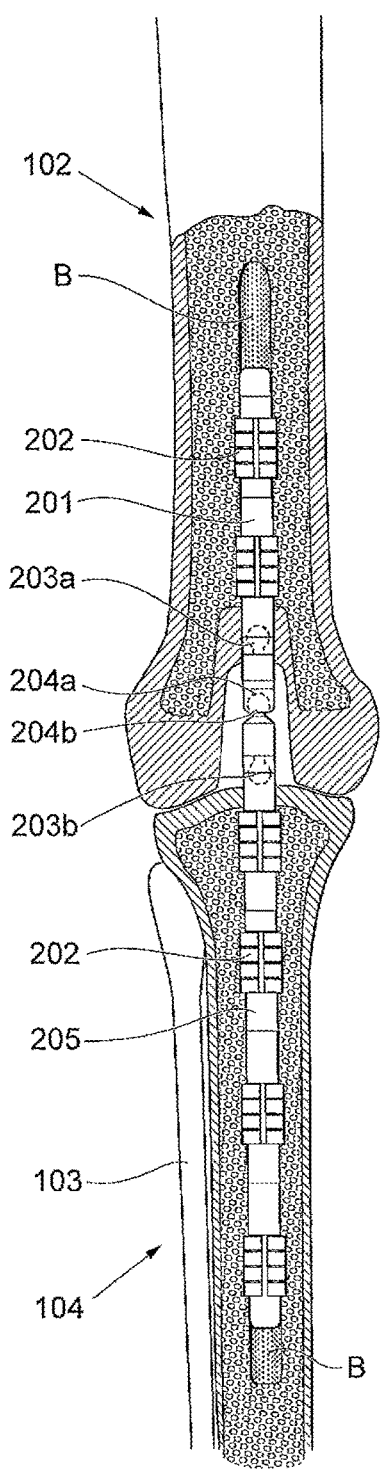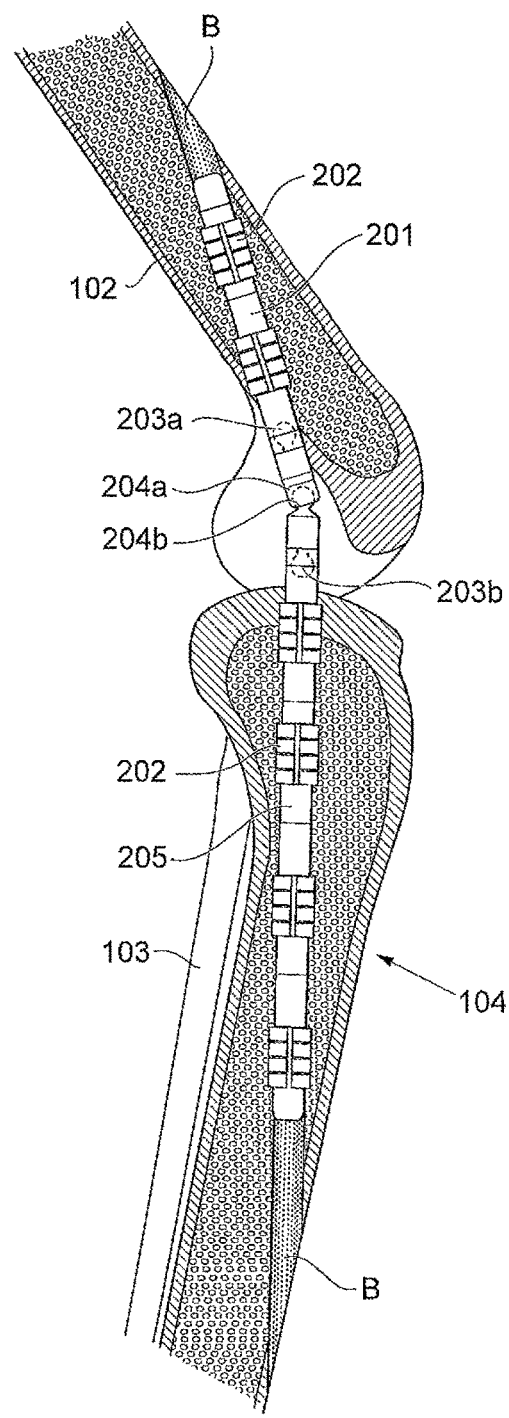

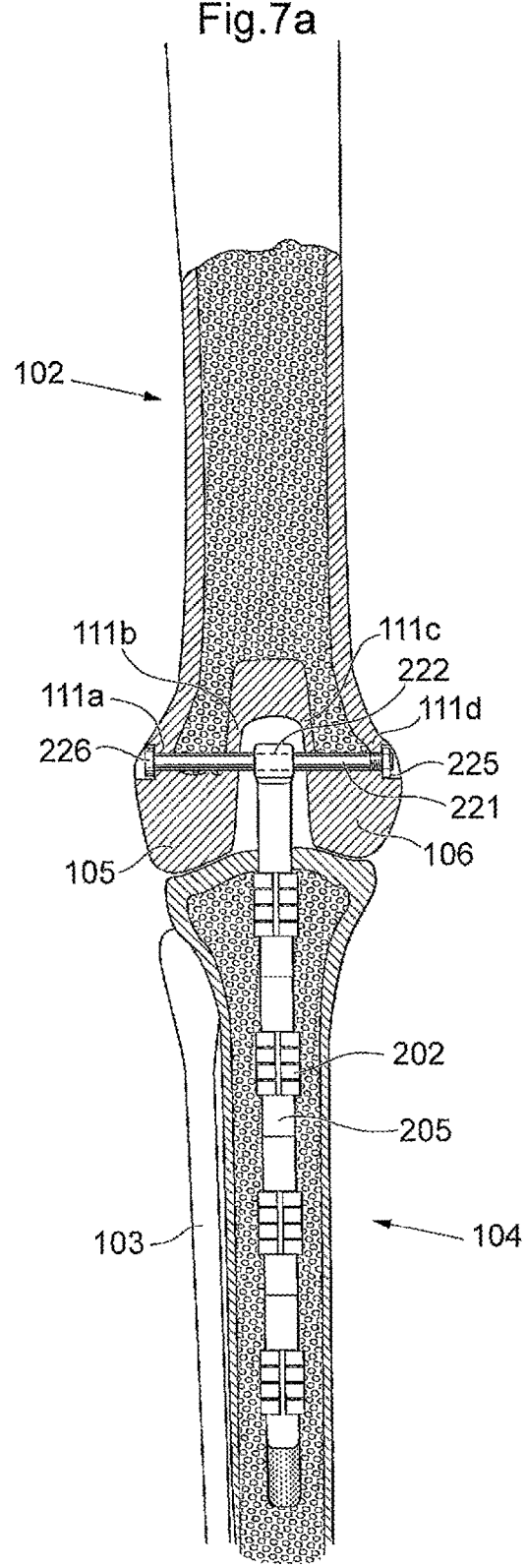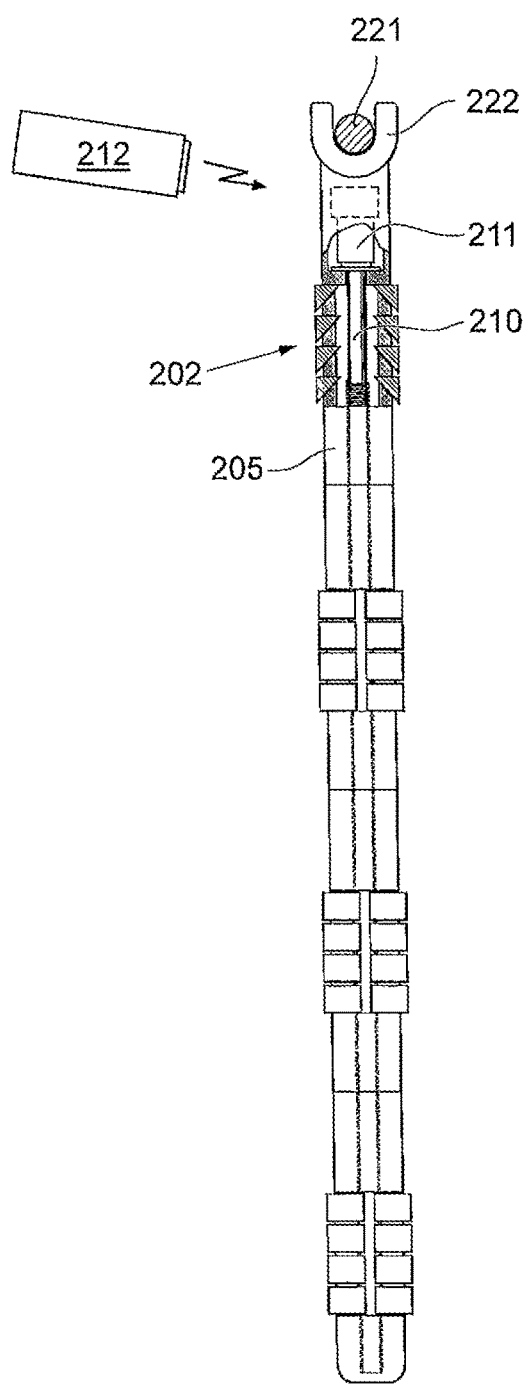

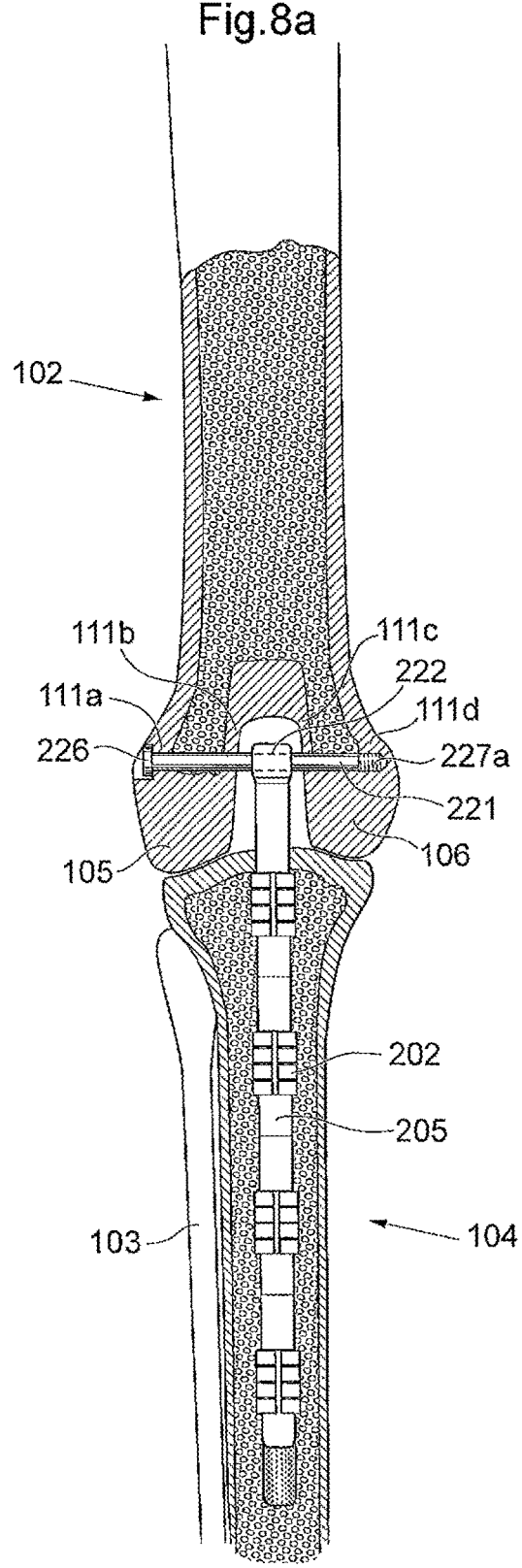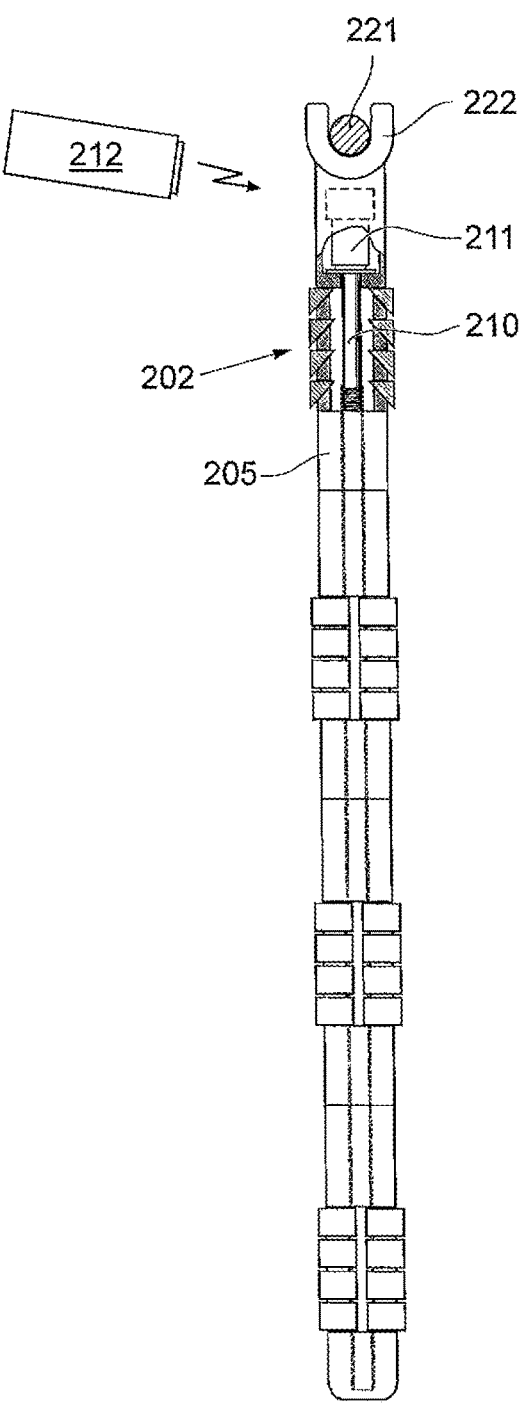

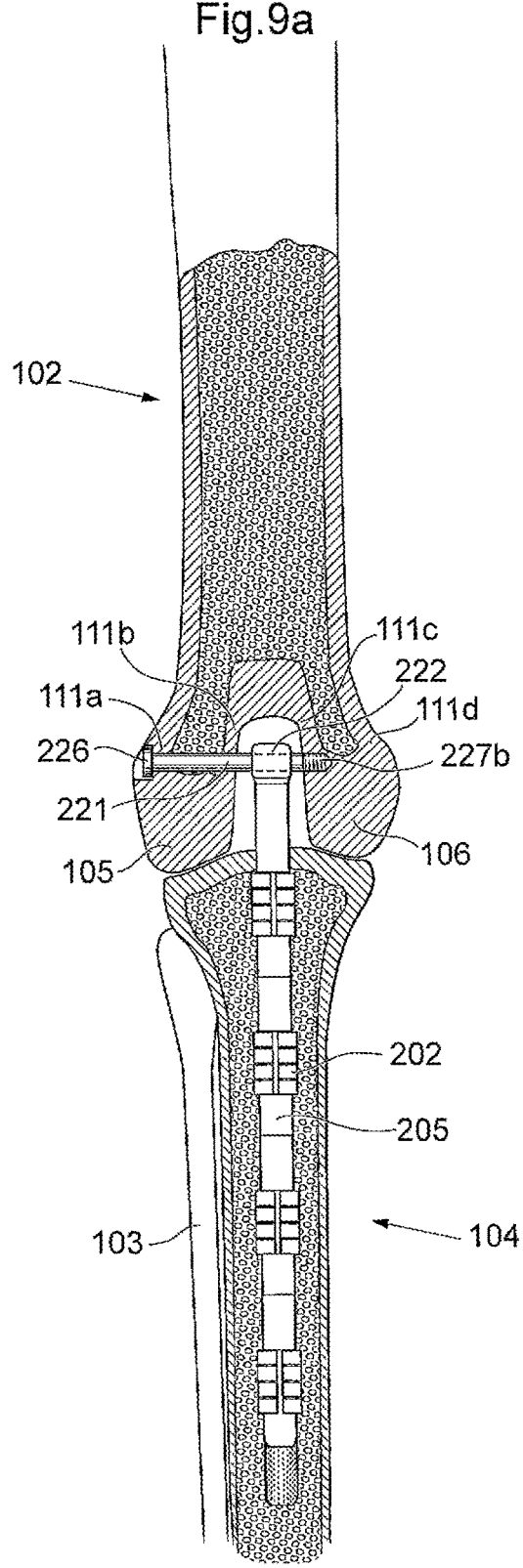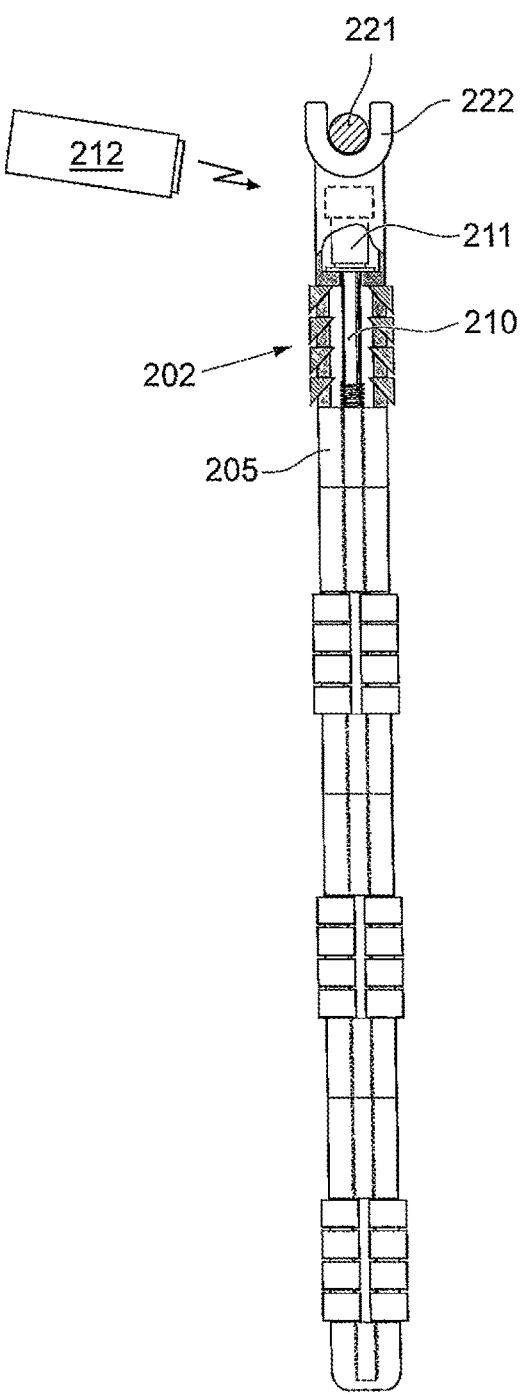

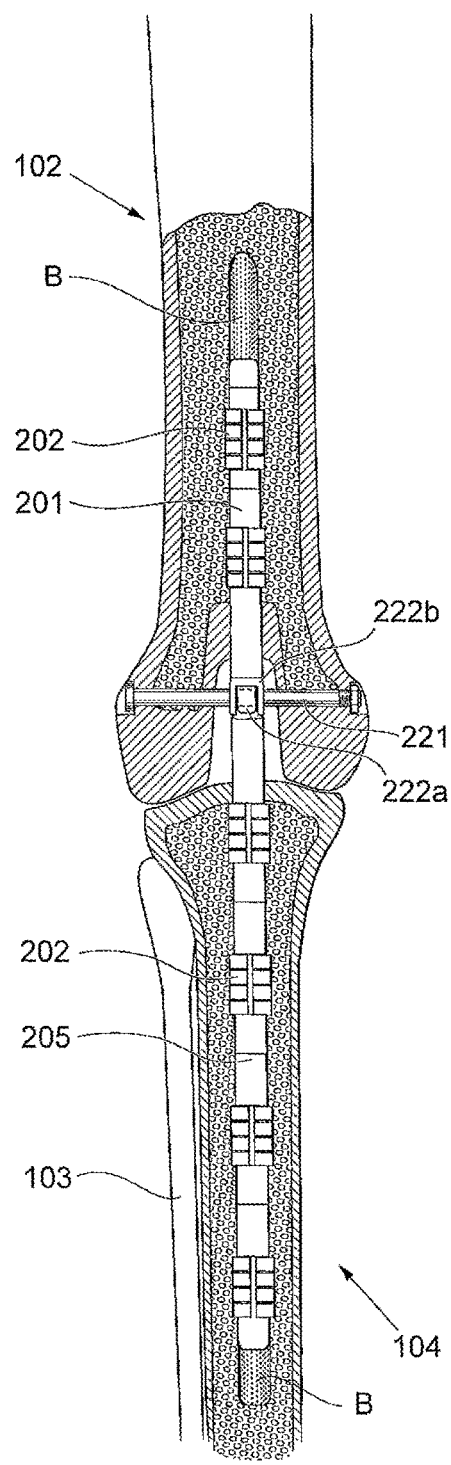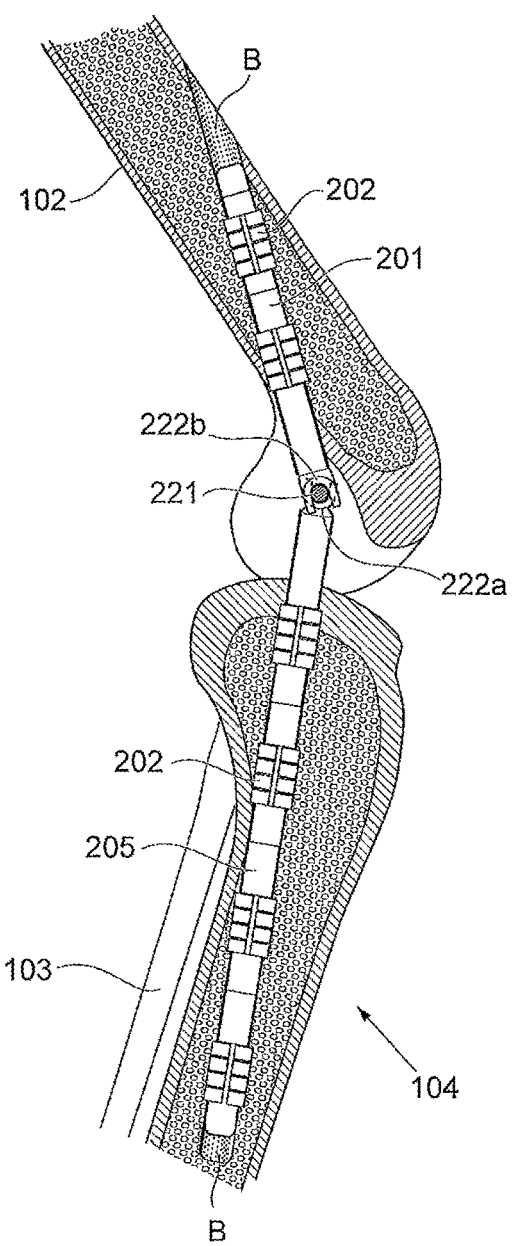

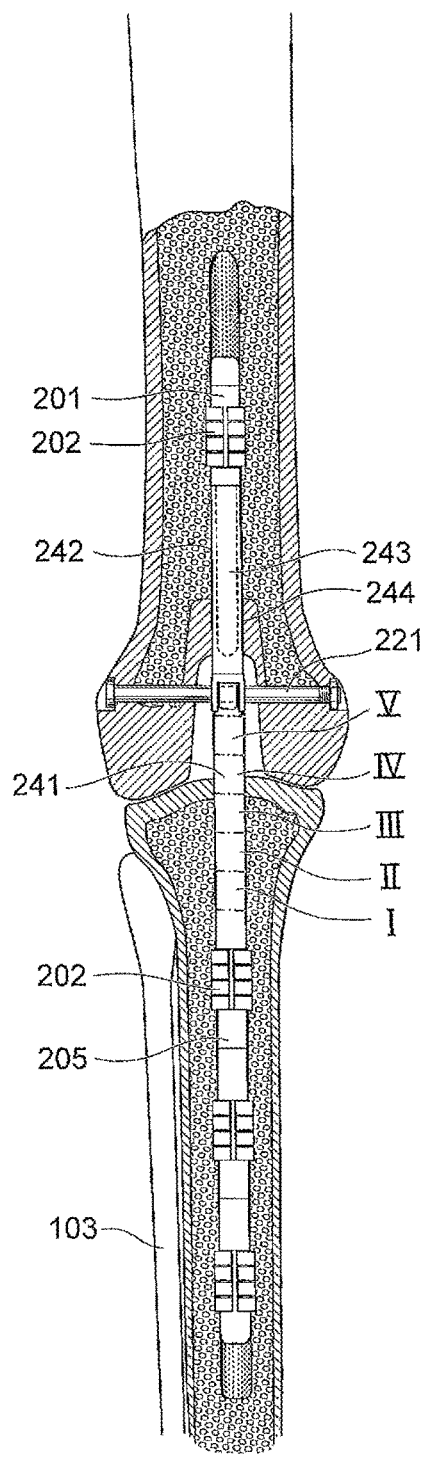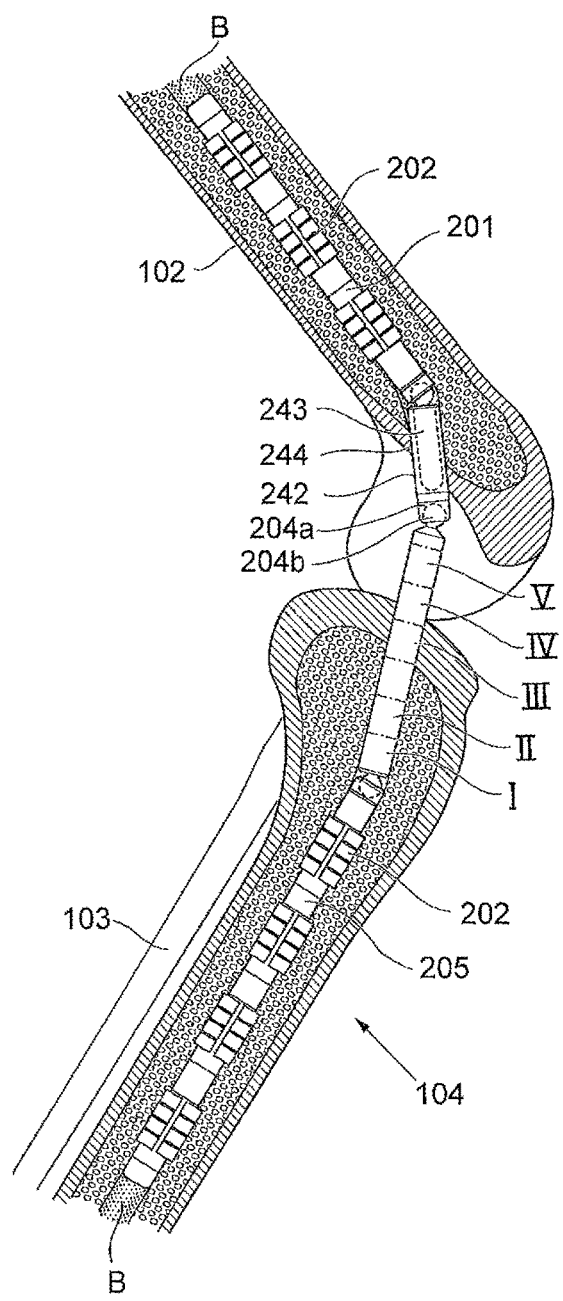

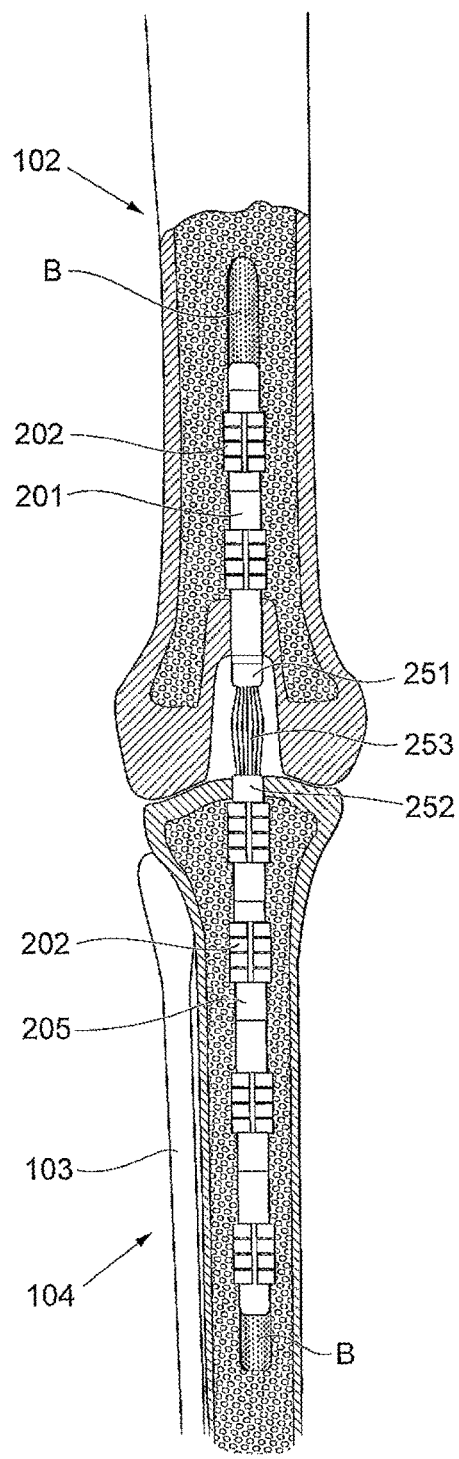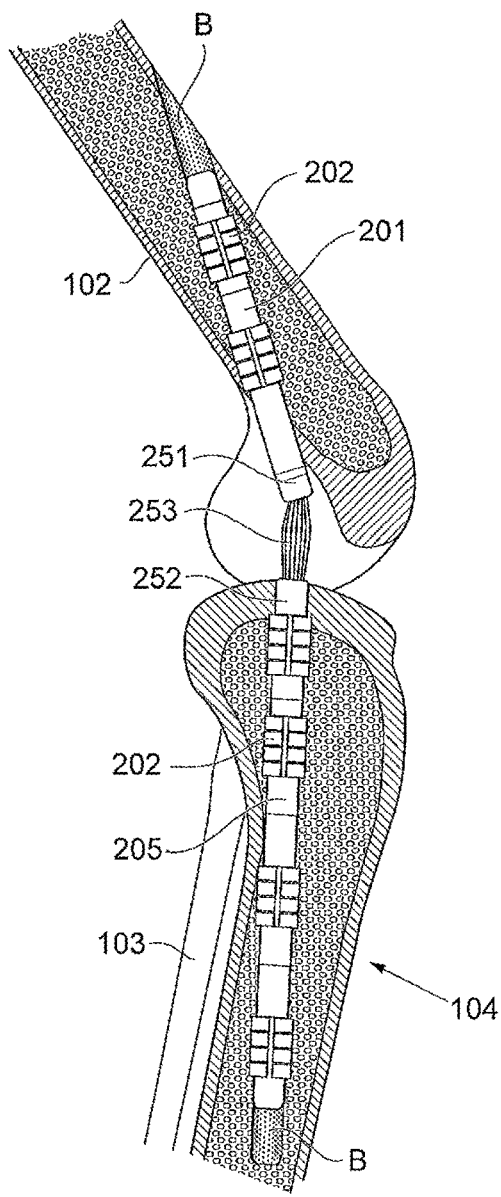

A-A

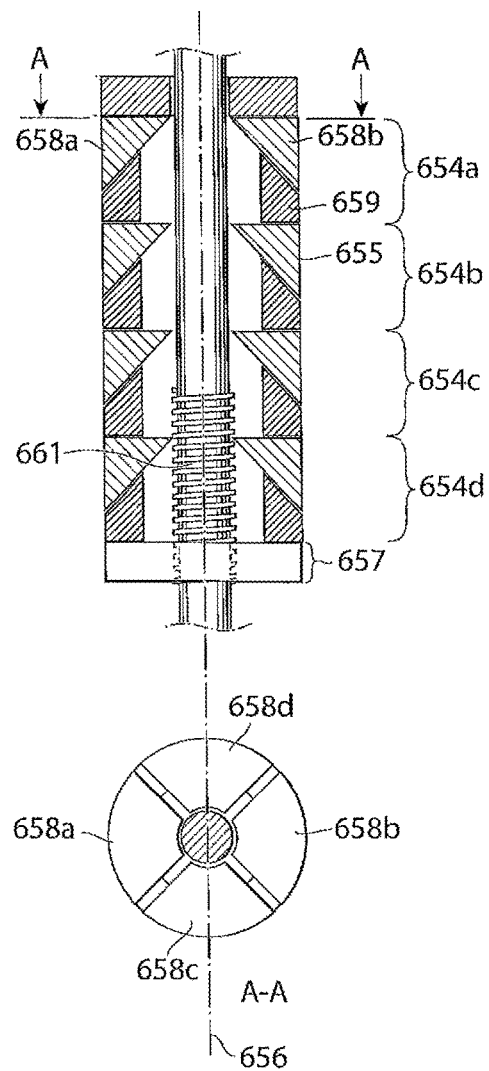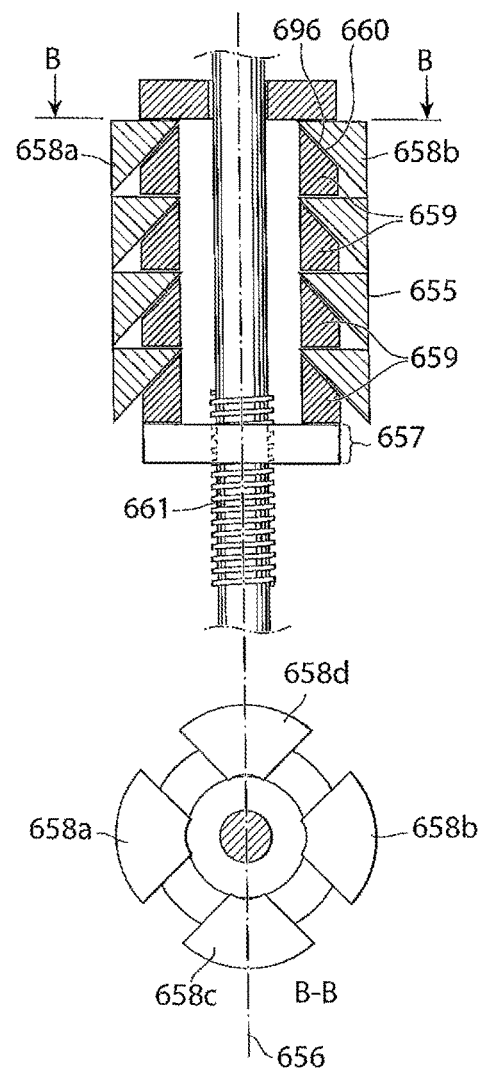

KNEE JOINT DEVICE

This application is the U.S. national phase of International Application No. PCT/SE2012/050004, filed 4 Jan. 2012, which designated the U.S. and claims priority from SE 1100012-2, filed 5 Jan. 2011, and SE 1100011-4, filed 5 Jan. 2011, the entire contents of each of which are incorporated herein by reference.

FIELD OF INVENTION

The present invention relates generally to a medical device for implantation in a human patient.

BACKGROUND

Knee replacement surgery is one of the most commons surgical procedures to date performed at more than a million patients every year worldwide. The most common reason for performing a knee replacement surgery is that the patient suffers from knee joint osteoarthritis, which is a syndrome in which a low-grade inflammation results in pain in the joints. The low-grade inflammation is caused by abnormal wearing of the cartilage that covers and acts as a cushion inside joints, which results in a decrease of the synovial fluid that lubricates the knee joint.

In conventional surgery the surgeon places a prosthesis on the lateral condyle, the medial condyle or both the medial and the lateral condyle. The prosthesis could further more comprise a contacting surface placed on the top part of the tibia bone and an artificial part replacing the knee cap.

The procedure usually takes up to two hours and the surgeon will make a single cut (10 to 30 cm long) down the front of the knee. The kneecap is moved to one side to reach the knee joint. The worn or damaged surfaces are removed and the bone are shaped to fit the artificial knee joint.

The average patient age is between 65 and 75. Of these surgeries, approximately 80% are unilateral (only one knee replaced) and 20% are bilateral.

The knee joint comprises proximal contacting surfaces, being sections of the medial condyle, the lateral condyle and an area of the femoral bone between the medial and the lateral condyle and a distal contacting surface being a cross-section of the proximal part of the tibia bone. Furthermore the knee joint comprises the patella which is a, triangular bone which articulates with the femur and covers and protect the knee joint. The knee joint also comprises the minisci which are cartilaginous elements within the knee joint which serve to protect the ends of the bones from rubbing on each other. The minisci also acts as shock absorbers in the knee. There are two menisci in each knee, the medial meniscus and the lateral meniscus.

Osteoarthritis is a common condition of cartilage failure that can lead to limited range of motion, bone damage and invariably, pain. Due to a combination of acute stress and chronic fatigue, osteoarthritis directly manifests itself in a wearing away of the articulating surface and, in extreme cases, bone can be exposed in the joint. Some additional examples of cartilage failure mechanisms include cellular matrix linkage rupture, chondrocyte protein synthesis inhibition, and chondrocyte apoptosis.

SUMMARY

A medical device for implantation in a knee joint of a human patient is provided. The medical device comprising: a transversal member adapted to be placed through at least three layers of cortical bone of the distal portion of the femoral bone, out of totally four cortical layers along a prolongation of the transversal member. The transversal member could be adapted to be involved in an artificial knee joint or artificial cruciate ligament, and the transversal member could comprise at least one fixation portion adapted to be involved in fixation of the transversal member to at least one of the at least four layers of femoral cortical bone. By providing a transversal member, a stable fixation to the femoral bone is provided.

According to one embodiment, the transversal member is adapted to be involved in the artificial joint positioned between the lateral and medial condyle and/or positioned between the normal lateral and medial joint surfaces and/or positioned cranial to the natural joint surfaces of the knee joint.

According to one embodiment, the transversal member is adapted to comprise the center of rotation of the artificial knee joint.

According to one embodiment, the transversal member is adapted to be placed through four layers of cortical bone of the distal portion of the femoral bone.

According to one embodiment, the transversal member comprises an artificial knee joint surface adapted to articulate with another artificial knee joint surface fixated to the tibial bone.

According to one embodiment, the transversal member comprises an artificial knee joint holding part adapted to be involved in holding the artificial knee joint.

According to one embodiment, the transversal member is adapted to be placed through three layers of cortical bone of the distal portion of the femoral bone and be fixated to a fourth layer of cortical bone of the distal portion of the femoral bone.

According to one embodiment, the transversal member is adapted to: be placed through two layers of cortical bone of a first condyle of the distal portion of the femoral bone, be placed through an artificial knee joint element fixated to the tibial bone, and be placed through or fixated in at least a third layer of cortical bone of the second condyle of the distal portion of the femoral bone.

According to one embodiment, the transversal member is adapted to: be placed through two layers of cortical bone of a first condyle of the distal portion of the femoral bone, be placed through an artificial knee joint element fixated to the tibial bone, be placed through a third layer of cortical bone of the second condyle of the distal portion of the femoral bone, and be placed through or fixated in a fourth layer of cortical bone of the second condyle of the distal portion of the femoral bone.

According to one embodiment, the transversal member is adapted to be connected to a femoral anchoring member in an area between the medial and lateral condyles, which could provide additional stability in the joint.

According to one embodiment, the transversal member is adapted to be connected to a tibial anchoring member in an area between the medial and lateral condyles, which could provide additional stability in the joint.

According to one embodiment, the artificial knee joint could comprise the connection between the transversal member and the tibial anchoring member.

According to one embodiment, the medical device could comprise at least one artificial cruciate ligament adapted to be fixated to the transversal member at a first cruciate ligament end.

According to one embodiment, a second cruciate ligament end could be placed on the opposite end to the first cruciate ligament end be adapted to be mounted through a bone channel in the tibial bone and adapted to be fixated to the bone on the inside or after passing to the outside of the bone channel, when implanted.

According to one embodiment, the medical device could comprise a tibial anchoring member adapted to be placed and anchor in the tibial bone, wherein a second cruciate ligament end could be placed on the opposite end to the first cruciate ligament end be adapted to be mounted to the tibial anchoring member, when implanted.

According to one embodiment, the transversal member is adapted to connect to an artificial knee joint surface at the lateral condyle of the femur.

According to one embodiment, the transversal member is adapted to connect to an artificial knee joint surface at the medial condyle of the femur.

According to one embodiment, the medical device comprises an artificial knee joint surface adapted to be placed at the lateral condyle of the femur.

According to one embodiment, the medical device according to any one of the preceding claims, comprises an artificial knee joint surface adapted to place at the medial condyle of the femur.

According to one embodiment, the medical device further comprises two artificial cruciate ligaments, the anterior and posterior cruciate ligament, adapted to be fixated to the transversal member at least one of; the same or different positions on the transversal member.

According to one embodiment, the transversal member have an elongated part, elongated in the anterior and posterior direction adapted to be placed between the medial condyle to accommodate the different positions of the cruciate ligaments.

A medical device for implantation in a knee joint of a human patient is provided. The medical device comprises at least one bone anchoring device, comprising at least one of; a tibial bone anchoring device adapted to be introduced through the cortical tibia bone into the bone marrow of the tibia bone at an area distal to the knee joint, and a femoral bone anchoring device, adapted to be introduced through the cortical femur bone into the bone marrow of the femur bone at an area proximal to the knee joint. The bone anchoring device is further adapted to exit the bone marrow through the cortical bone at an area site inside the normal knee joint, wherein the bone anchoring device comprises at least one of; a support for at least one artificial knee joint surface, a support for at least one artificial knee joint cruciate ligament, and at least one artificial knee joint surface for creating at least a part of an artificial knee joint. By providing a bone anchoring device a stable fixation could be created.

According to one embodiment, the tibial bone anchoring device could be adapted to be connected to a second femoral bone anchoring device and adapted to pass the femoral cortical bone only on a site placed inside the normal knee joint, the medical device could further comprise at least one artificial knee joint movable connecting the tibial and femoral bone anchoring device.

According to one embodiment, the femoral bone anchoring device is adapted to be connected to a second tibial bone anchoring device and adapted to pass the tibial cortical bone only on a site placed inside the normal knee joint, the medical device further comprises at least one artificial knee joint movable connecting the tibial and femoral bone anchoring device.

According to one embodiment the medical device further comprises at least one artificial knee joint, movably connected to the tibial anchoring device and the femoral bone anchoring device.

According to one embodiment the femoral bone anchoring device and the tibial bone anchoring device are adapted to be movably connected to each other for forming an artificial knee joint.

According to one embodiment, the tibial bone anchoring device further comprises a second joint allowing movement between a first and second portion of the tibial bone anchoring device.

According to one embodiment, the first portion of the tibial bone anchoring device is a anchoring portion, and the second portion of the tibial bone anchoring device is a support portion for at least one of; supporting the artificial knee joint surface, supporting the at least one artificial knee joint cruciate ligament, and comprising at least one artificial knee joint surface.

According to one embodiment, the femoral bone anchoring device further comprises a second joint allowing movement between a first and second portion of the femoral bone anchoring device.

According to one embodiment, the first portion of the femoral bone anchoring device is a anchoring portion, and wherein the second portion of the femoral bone anchoring device is a support portion for supporting at least one of; the artificial knee joint surface, the at least one artificial knee joint cruciate ligament, and the at least one artificial knee joint surface.

According to one embodiment, the artificial knee joint and the second joint are adapted to be adjustable for adjusting the angle or position of the artificial knee joint support, cruciate ligament support or artificial knee joint surface.

According to one embodiment, a normal knee joint surfaces are placed both at the medial and lateral femoral condyle, wherein the artificial knee joint is adapted to be placed between the normal lateral and medial joint surfaces, when implanted.

According to one embodiment, a normal knee joint surfaces are placed between the tibial and femoral bones both at the medial and lateral femoral condyle, wherein the artificial knee joint is adapted to be placed more cranial than the normal lateral and medial joint surfaces, when implanted.

According to one embodiment, the medical device comprises a transversal member adapted to be placed through at least two layers of femoral cortical bone involving both femoral condyles, wherein the transversal member comprises at least one artificial knee joint or cruciate ligament holding part adapted to be involved in at least partly holding the artificial knee joint or artificial cruciate ligament.

According to one embodiment, the transversal member comprises at least one artificial knee joint surface.

According to one embodiment, the artificial knee joint is adapted to form one single artificial knee joint with two contacting joint surfaces adapted to replace both the two lateral contacting surfaces and the two medial contacting surfaces existing in normal knee joint, when implanted According to one embodiment, the part of the bone anchoring device placed in the bone marrow comprises, along one or more of an elongated portion thereof, at least one radius adjustment, adapted to adjust the maximum radius substantially transverse or at least clearly angled in relation to a center axis of the bone anchoring device, for fixating the bone anchoring device towards the cortical bone, from the inside of the bone along one or more of the elongated portions, when implanted in the bone marrow of the femur or tibia bone.

According to one embodiment, the part of the bone anchoring device placed in the bone marrow comprises cortical bone contacting surfaces adapted to contact the cortical bone from the inside of the tibia or femur bone, along one or more of an elongated portion thereof, wherein at least one of; the cortical bone contacting surfaces and the related material in the bone anchoring device, have a suspension in relation to the cortical bone, wherein the suspension comprising at least one of; a bendable part and an elastic part of the bone anchoring device, for a chock absorbing fixation of the bone anchoring device towards the cortical bone, along one or more of the elongated portions, when implanted in the bone marrow of the femur or tibia bone.

According to one embodiment, the medical device comprises a transversal member adapted to be placed through at least three layers of cortical bone of the distal portion of the femoral bone, out of totally four cortical layers in the elongation of the transversal member, wherein the transversal member comprises at least one fixation portion adapted to be involved in fixation of the transversal member to at least one of the at least four layers of femoral cortical bone, and wherein the transversal member is adapted to be involved in at least one of; the artificial knee joint and an artificial cruciate ligament support.

According to one embodiment, the transversal member is adapted to comprise the center of rotation of the artificial knee joint.

According to one embodiment, the transversal member comprises an artificial knee joint surface adapted to articulate with another artificial knee joint surface being part of the bone anchoring device.

According to one embodiment, the bone anchoring device is adapted to be able to drill in the tibia or femur bone.

According to one embodiment, the medical device further comprises at least one artificial cruciate ligament adapted to be fixated to the artificial cruciate ligament support with its first end.

According to one embodiment, a second cruciate ligament end, placed on the opposite end to the first cruciate ligament end, is adapted to be mounted through a bone channel in the tibial or femoral bone and adapted to be fixated to the bone at at least one of; the inside of the bone channel, and on the outside of the knee joint after passing through the bone channel, when implanted.

According to one embodiment the anterior and posterior cruciate ligament is adapted to be fixated to the artificial cruciate ligament support.

According to one embodiment, a knee joint has a femoral joint surface and a tibial joint surface both placed in the position of the medial femoral condyle and the lateral femoral condyle, wherein the bone anchoring device is adapted to support at least one artificial joint surface, being adapted to be positioned in at least one of the position of the lateral and medial femoral condyle and connected to the bone anchoring device.

According to one embodiment, at least one artificial joint surface is adapted to be positioned at least in one of the position of the lateral and medial femoral condyle and fixated to the bone anchoring device.

In any of the embodiments herein varying elasticity may play an important role as a tool for chock absorbing forces towards the bone. The construction may be done in many different ways to achieve the same goal. Preferable this construction will be combined with a radius adjustment devices according to any of the embodiments herein. The varying elasticity could be achieved using different technologies creating varying elasticity and the invention should not be limited to embodiments disclosed herein. Similar result as with the varying elasticity could also be achieved by any kind of suspension including spring suspension and the construction may also be bendable or flexible achieving the same result.

A medical device for implantation in a knee joint of a human patient is provided. The medical device comprises at least one bone anchoring device, comprising at least one of; a tibial bone anchoring device adapted to be introduced through the cortical tibia bone into the bone marrow of the tibia bone at an area distal to the knee joint, and a femoral bone anchoring device, adapted to be introduced through the cortical femur bone into the bone marrow of the femur bone at an area proximal to the knee joint. The bone anchoring device is further adapted to exit the bone marrow through the cortical bone at an area site inside the normal knee joint, wherein the bone anchoring device comprises at least one of; a support for at least one artificial knee joint surface, a support for at least one artificial knee joint cruciate ligament, and at least one artificial knee joint surface for creating at least a part of an artificial knee joint. By providing a bone anchoring device a stable fixation could be created.

According to one embodiment, the tibial bone anchoring device could be adapted to be connected to a second femoral bone anchoring device and adapted to pass the femoral cortical bone only on a site placed inside the normal knee joint, the medical device could further comprise at least one artificial knee joint movable connecting the tibial and femoral bone anchoring device.

According to one embodiment, the femoral bone anchoring device is adapted to be connected to a second tibial bone anchoring device and adapted to pass the tibial cortical bone only on a site placed inside the normal knee joint, the medical device further comprises at least one artificial knee joint movable connecting the tibial and femoral bone anchoring device.

According to one embodiment the medical device further comprises at least one artificial knee joint, movably connected to the tibial anchoring device and the femoral bone anchoring device.

According to one embodiment the femoral bone anchoring device and the tibial bone anchoring device are adapted to be movably connected to each other for forming an artificial knee joint.

According to one embodiment, the tibial bone anchoring device further comprises a second joint allowing movement between a first and second portion of the tibial bone anchoring device.

According to one embodiment, the first portion of the tibial bone anchoring device is a anchoring portion, and the second portion of the tibial bone anchoring device is a support portion for at least one of; supporting the artificial knee joint surface, supporting the at least one artificial knee joint cruciate ligament, and comprising at least one artificial knee joint surface.

According to one embodiment, the femoral bone anchoring device further comprises a second joint allowing movement between a first and second portion of the femoral bone anchoring device.

According to one embodiment, the first portion of the femoral bone anchoring device is a anchoring portion, and wherein the second portion of the femoral bone anchoring device is a support portion for supporting at least one of; the artificial knee joint surface, the at least one artificial knee joint cruciate ligament, and the at least one artificial knee joint surface.

According to one embodiment, the artificial knee joint and the second joint are adapted to be adjustable for adjusting the angle or position of the artificial knee joint support, cruciate ligament support or artificial knee joint surface.

According to one embodiment, a normal knee joint surfaces are placed both at the medial and lateral femoral condyle, wherein the artificial knee joint is adapted to be placed between the normal lateral and medial joint surfaces, when implanted.

According to one embodiment, a normal knee joint surfaces are placed between the tibial and femoral bones both at the medial and lateral femoral condyle, wherein the artificial knee joint is adapted to be placed more cranial than the normal lateral and medial joint surfaces, when implanted.

According to one embodiment, the medical device comprises a transversal member adapted to be placed through at least two layers of femoral cortical bone involving both femoral condyles, wherein the transversal member comprises at least one artificial knee joint or cruciate ligament holding part adapted to be involved in at least partly holding the artificial knee joint or artificial cruciate ligament.

According to one embodiment, the transversal member comprises at least one artificial knee joint surface.

According to one embodiment, the artificial knee joint is adapted to form one single artificial knee joint with two contacting joint surfaces adapted to replace both the two lateral contacting surfaces and the two medial contacting surfaces existing in normal knee joint, when implanted According to one embodiment, the part of the bone anchoring device placed in the bone marrow comprises, along one or more of an elongated portion thereof, at least one radius adjustment, adapted to adjust the maximum radius substantially transverse or at least clearly angled in relation to a center axis of the bone anchoring device, for fixating the bone anchoring device towards the cortical bone, from the inside of the bone along one or more of the elongated portions, when implanted in the bone marrow of the femur or tibia bone.

According to one embodiment, the part of the bone anchoring device placed in the bone marrow comprises cortical bone contacting surfaces adapted to contact the cortical bone from the inside of the tibia or femur bone, along one or more of an elongated portion thereof, wherein at least one of; the cortical bone contacting surfaces and the related material in the bone anchoring device, have a suspension in relation to the cortical bone, wherein the suspension comprising at least one of; a bendable part and an elastic part of the bone anchoring device, for a chock absorbing fixation of the bone anchoring device towards the cortical bone, along one or more of the elongated portions, when implanted in the bone marrow of the femur or tibia bone.

According to one embodiment, the medical device comprises a transversal member adapted to be placed through at least three layers of cortical bone of the distal portion of the femoral bone, out of totally four cortical layers in the elongation of the transversal member, wherein the transversal member comprises at least one fixation portion adapted to be involved in fixation of the transversal member to at least one of the at least four layers of femoral cortical bone, and wherein the transversal member is adapted to be involved in at least one of; the artificial knee joint and an artificial cruciate ligament support.

According to one embodiment, the transversal member is adapted to comprise the center of rotation of the artificial knee joint.

According to one embodiment, the transversal member comprises an artificial knee joint surface adapted to articulate with another artificial knee joint surface being part of the bone anchoring device.

According to one embodiment, the bone anchoring device is adapted to be able to drill in the tibia or femur bone.

According to one embodiment, the medical device further comprises at least one artificial cruciate ligament adapted to be fixated to the artificial cruciate ligament support with its first end.

According to one embodiment, a second cruciate ligament end, placed on the opposite end to the first cruciate ligament end, is adapted to be mounted through a bone channel in the tibial or femoral bone and adapted to be fixated to the bone at at least one of; the inside of the bone channel, and on the outside of the knee joint after passing through the bone channel, when implanted.

According to one embodiment the anterior and posterior cruciate ligament is adapted to be fixated to the artificial cruciate ligament support.

According to one embodiment, a knee joint has a femoral joint surface and a tibial joint surface both placed in the position of the medial femoral condyle and the lateral femoral condyle, wherein the bone anchoring device is adapted to support at least one artificial joint surface, being adapted to be positioned in at least one of the position of the lateral and medial femoral condyle and connected to the bone anchoring device.

According to one embodiment, at least one artificial joint surface is adapted to be positioned at least in one of the position of the lateral and medial femoral condyle and fixated to the bone anchoring device.

A medical device for implantation in a knee joint of a human patient is further provided. The medical device comprising: a transversal member adapted to be placed through at least three layers of cortical bone of the distal portion of the femoral bone, out of totally four cortical layers along a prolongation of the transversal member. The transversal member could be adapted to be involved in an artificial knee joint or artificial cruciate ligament, and the transversal member could comprise at least one fixation portion adapted to be involved in fixation of the transversal member to at least one of the at least four layers of femoral cortical bone. By providing a transversal member, a stable fixation to the femoral bone is provided.

According to one embodiment, the transversal member is adapted to be involved in the artificial joint positioned between the lateral and medial condyle and/or positioned between the normal lateral and medial joint surfaces and/or positioned cranial to the natural joint surfaces of the knee joint.

According to one embodiment, the transversal member is adapted to comprise the center of rotation of the artificial knee joint.

According to one embodiment, the transversal member is adapted to be placed through four layers of cortical bone of the distal portion of the femoral bone.

According to one embodiment, the transversal member comprises an artificial knee joint surface adapted to articulate with another artificial knee joint surface fixated to the tibial bone.

According to one embodiment, the transversal member comprises an artificial knee joint holding part adapted to be involved in holding the artificial knee joint.

According to one embodiment, the transversal member is adapted to be placed through three layers of cortical bone of the distal portion of the femoral bone and be fixated to a fourth layer of cortical bone of the distal portion of the femoral bone.

According to one embodiment, the transversal member is adapted to: be placed through two layers of cortical bone of a first condyle of the distal portion of the femoral bone, be placed through an artificial knee joint element fixated to the tibial bone, and be placed through or fixated in at least a third layer of cortical bone of the second condyle of the distal portion of the femoral bone.

According to one embodiment, the transversal member is adapted to: be placed through two layers of cortical bone of a first condyle of the distal portion of the femoral bone, be placed through an artificial knee joint element fixated to the tibial bone, be placed through a third layer of cortical bone of the second condyle of the distal portion of the femoral bone, and be placed through or fixated in a fourth layer of cortical bone of the second condyle of the distal portion of the femoral bone.

According to one embodiment, the transversal member is adapted to be connected to a femoral anchoring member in an area between the medial and lateral condyles, which could provide additional stability in the joint.

According to one embodiment, the transversal member is adapted to be connected to a tibial anchoring member in an area between the medial and lateral condyles, which could provide additional stability in the joint.

According to one embodiment, the artificial knee joint could comprise the connection between the transversal member and the tibial anchoring member.

According to one embodiment, the medical device could comprise at least one artificial cruciate ligament adapted to be fixated to the transversal member at a first cruciate ligament end.

According to one embodiment, a second cruciate ligament end could be placed on the opposite end to the first cruciate ligament end be adapted to be mounted through a bone channel in the tibial bone and adapted to be fixated to the bone on the inside or after passing to the outside of the bone channel, when implanted.

According to one embodiment, the medical device could comprise a tibial anchoring member adapted to be placed and anchor in the tibial bone, wherein a second cruciate ligament end could be placed on the opposite end to the first cruciate ligament end be adapted to be mounted to the tibial anchoring member, when implanted.

According to one embodiment, the transversal member is adapted to connect to an artificial knee joint surface at the lateral condyle of the femur.

According to one embodiment, the transversal member is adapted to connect to an artificial knee joint surface at the medial condyle of the femur.

According to one embodiment, the medical device comprises an artificial knee joint surface adapted to be placed at the lateral condyle of the femur.

According to one embodiment, the medical device according to any one of the preceding claims, comprises an artificial knee joint surface adapted to place at the medial condyle of the femur.

According to one embodiment, the medical device further comprises two artificial cruciate ligaments, the anterior and posterior cruciate ligament, adapted to be fixated to the transversal member at least one of; the same or different positions on the transversal member.

According to one embodiment, the transversal member have an elongated part, elongated in the anterior and posterior direction adapted to be placed between the medial condyle to accommodate the different positions of the cruciate ligaments.

In any of the embodiments herein varying elasticity may play an important role as a tool for chock absorbing forces towards the bone. The construction may be done in many different ways to achieve the same goal. Preferable this construction will be combined with a radius adjustment devices according to any of the embodiments herein. The varying elasticity could be achieved using different technologies creating varying elasticity and the invention should not be limited to embodiments disclosed herein. Similar result as with the varying elasticity could also be achieved by any kind of suspension including spring suspension and the construction may also be bendable or flexible achieving the same result.

Please note that any embodiment or part of embodiment, feature, method, associated system, part of system described herein may be combined in any way.

BRIEF DESCRIPTION OF DRAWINGS

The invention is now described, by way of example, with reference to the accompanying drawings, in which:

FIG. 4*a* shows a posterior view of a leg of a patient in section, FIG. 4*b* shows a side view of a leg of a patent in section, FIG. 7*a* shows a posterior view of a leg of a patient in section, when a medical device according to one embodiment has been implanted, FIG. 7*b* shows a bone anchoring device according to one embodiment in further detail, FIG. 8*a* shows a posterior view of a leg of a patient in section, when a medical device according to one embodiment has been implanted, FIG. 8*b* shows a bone anchoring device according to one embodiment in further detail, FIG. 9*a* shows a posterior view of a leg of a patient in section, when a medical device according to one embodiment has been implanted, FIG. 9*b* shows a bone anchoring device according to one embodiment in further detail, FIG. 10*a* shows a posterior view of a leg of a patient in section, when a medical device according to one embodiment has been implanted, FIG. 10*b* shows a side view of a leg of a patent in section when a medical device according to one embodiment has been implanted, FIG. 12a shows a posterior view of a leg of a patient in section, when a medical device according to one embodiment has been implanted, FIG. 12b shows a side view of a leg of a patent in section when a medical device according to one embodiment has been implanted, FIG. 13a shows a posterior view of a leg of a patient in section, when an artificial cruciate ligament has been implanted, FIG. 13b shows a side view of a leg of a patent in section, when an artificial cruciate ligament has been implanted, FIG. 19a shows a radius adjustment member according to one embodiment in further detail, in a first state, FIG. 19b shows a radius adjustment member according to one embodiment in further detail, in a second state.

DETAILED DESCRIPTION

Figure 1:
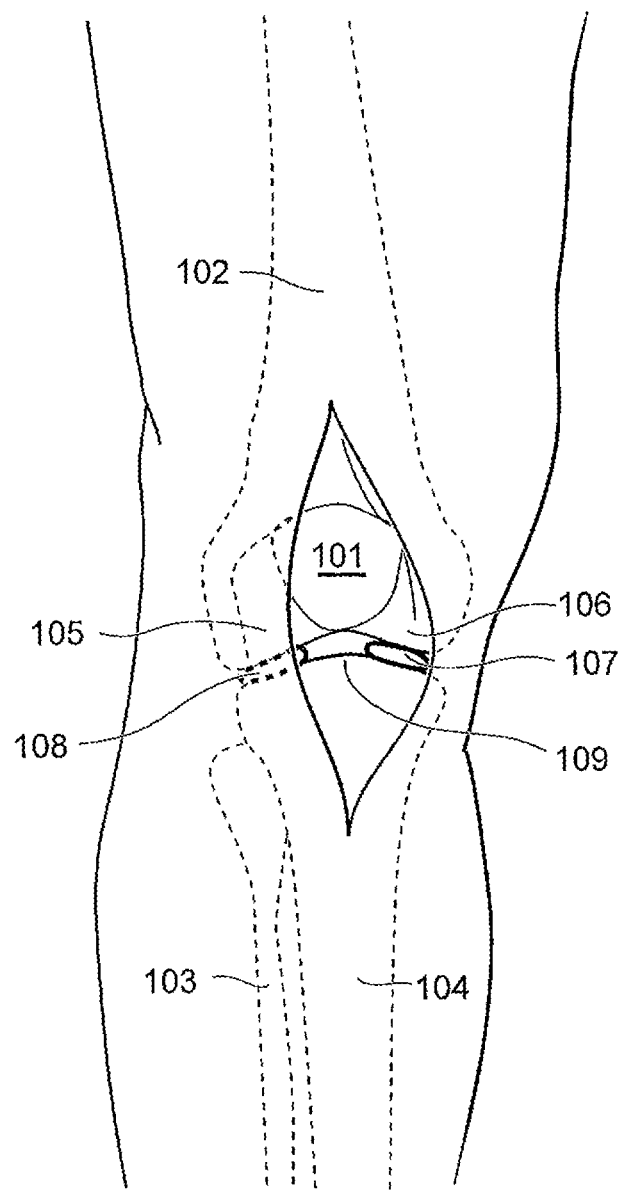
FIG. 1 shows an anterior view of the right leg of a human patient when an incision in a surgical method has been performed.

The anatomy of the hip joint and its surroundings is further disclosed in: Marieb et al., Human Anatomy, 2003, Benjamin Cummings, San Francisco, pages 195-202 and in Moore et al., Clinically oriented anatomy, 1999, Lippincott, Williams & Wilkins, Baltimore, pages 501-653, both hereby incorporated by reference.

A length axis of the femoral bone is to be understood as an axis which extends in the direction of the length of the femoral bone from the proximal part of the femoral bone to the distal part of the femoral bone.

An axis of the lateral condyle and the medial condyle is to be understood as an axis which is perpendicular to a length axis of the femoral bone. The functional knee movements of a natural knee joint are performed in around an axis of the lateral and medial condyle.

Biocompatible material is to be understood as being a material with low level of immune response. Biocompatible materials are sometimes also referred to as biomaterials. Analogous is biocompatible metals a biocompatible metal with low immune response such as titanium or tantalum. The biocompatible metal could also be a biocompatible alloy comprising at least one biocompatible metal.

A metal alloy is to be understood as a mixture of two or more elements in solid solution in which the major component is a metal. A steel alloy is hence an alloy wherein one of the components is steel which in turn is an alloy of iron and carbon. A titanium alloy is hence an alloy wherein one of the components is titanium.

Elasticity is to be understood as a materials ability to deform in an elastic way.

Carrying surface and weight carrying surface is to be understood as a surface adapted to carry weight inside of said knee joint.

Functional knee movements are to be understood as movements of the knee that at least partly correspond to the natural movements of the knee. On some occasions the natural movements of the knee joint might be somewhat limited or altered after knee joint surgery, which makes the functional knee movements of a knee joint with artificial surfaces somewhat different than the functional knee movements of a natural knee joint.

The functional position of an implantable medical device or prosthesis is the position in which the knee joint can perform functional knee movements.

Functional knee joint is a knee joint that can perform functional knee movements either with or without an implanted medical device or prosthesis.

Full functional size is to be understood as the size of the medical device when said medical device is implanted in the knee joint.

The medical device according to any of the embodiments could comprise at least one material selected from a group consisting of polytetrafluoro ethylene (PTFE), perfluoroalkoxy (PFA) and fluorinated ethylene propylene (FEP). It is furthermore conceivable that the material comprises a metal alloy, such as cobalt-chromium-molybdenum or titanium or stainless steel, or polyethylene, such as cross-linked polyethylene or gas sterilized polyethylene. The use of ceramic material is also conceivable, in the contacting surfaces or the entire medical device such as zirconium or zirconium dioxide ceramics or alumina ceramics. The part of the medical device in contact with human bone for fixation of the medical device to human bone could comprise a poorhouse structure which could be a porous micro or nano-structure adapted to promote the growth-in of human bone in the medical device for fixating the medical device. The porous structure could be achieved by applying a hydroxy-apatite (HA) coating, or a rough open-pored titanium coating, which could be produced by air plasma spraying, a combination comprising a rough open-pored titanium coating and a HA top layer is also conceivable. The articulating surfaces could be made of a self lubricated material such as a waxy polymer, such as PTFE, WA, PEP, FE and UMWPE, or a powder metallurgy material which could be infused with a lubricant, which preferably is a biocompatible lubricant such as a Hyaluronic acid derivate. It is also conceivable that the material of contacting parts or surfaces of the medical device herein is adapted to be constantly or intermittently lubricated. According to some embodiments the parts or portions of the medical device could comprise a combination of metal materials and/or carbon fibers and/or boron, a combination of metal and plastic materials, a combination of metal and carbon based material, a combination of carbon and plastic based material, a combination of flexible and stiff materials, a combination of elastic and less elastic materials, Corian or acrylic polymers.

In the following a detailed description of embodiments will be given. In the drawing figures, like reference numerals designate identical or corresponding elements throughout the several figures. It will be appreciated that these figures are for illustration only and are not in any way restricting the scope of the invention. Thus, any references to direction, such as "up" or "down", are only referring to the directions shown in the figures. Also, any dimensions etc. shown in the figures are for illustration purposes.

FIG. 1 shows the right leg of a human patient. The femoral bone 102 having a distal part comprising the lateral condyle 105, the medial condyle 106 and an area between said lateral and said medial condyle 109. The sections of the distal part of the femoral bone 102 comprises contacting surfaces of the knee joint. The knee joint furthermore comprises the patella 101, which is a triangular bone which articulates with the femur 102 and covers and protect the knee joint. The knee joint also comprises the minisci 107, 108 which are cartilaginous elements within the knee joint which serve as articulating surfaces to protect the ends of the bones from rubbing on each other. The minisci 107, 108 also acts as shock absorbers in the knee joint, to absorb the shocks from the movement of the human patient. There are two menisci 107, 108 in each knee, the medial meniscus 107 and the lateral meniscus 108. In patients with osteoarthritis, the menisci 107, 108 which acts as articulating surfaces i.e. weight carrying surfaces are worn away and, in extreme cases, bone can be exposed in the joint. The knee joint is protected by the knee joint capsule 132 also known as the articular capsule of the knee joint or the capsular ligament of the knee joint. The knee joint capsule 132 is wide and lax; thin in front and at the side; and contains the patella 101, ligaments, minisci 107,108, and bursae, which are small fluid-filled sacs made of white fibrous tissue. The knee joint capsule 132 consists of a synovial and a fibrous membrane separated by fatty deposits anteriorly and posteriorly.

Figure 2:
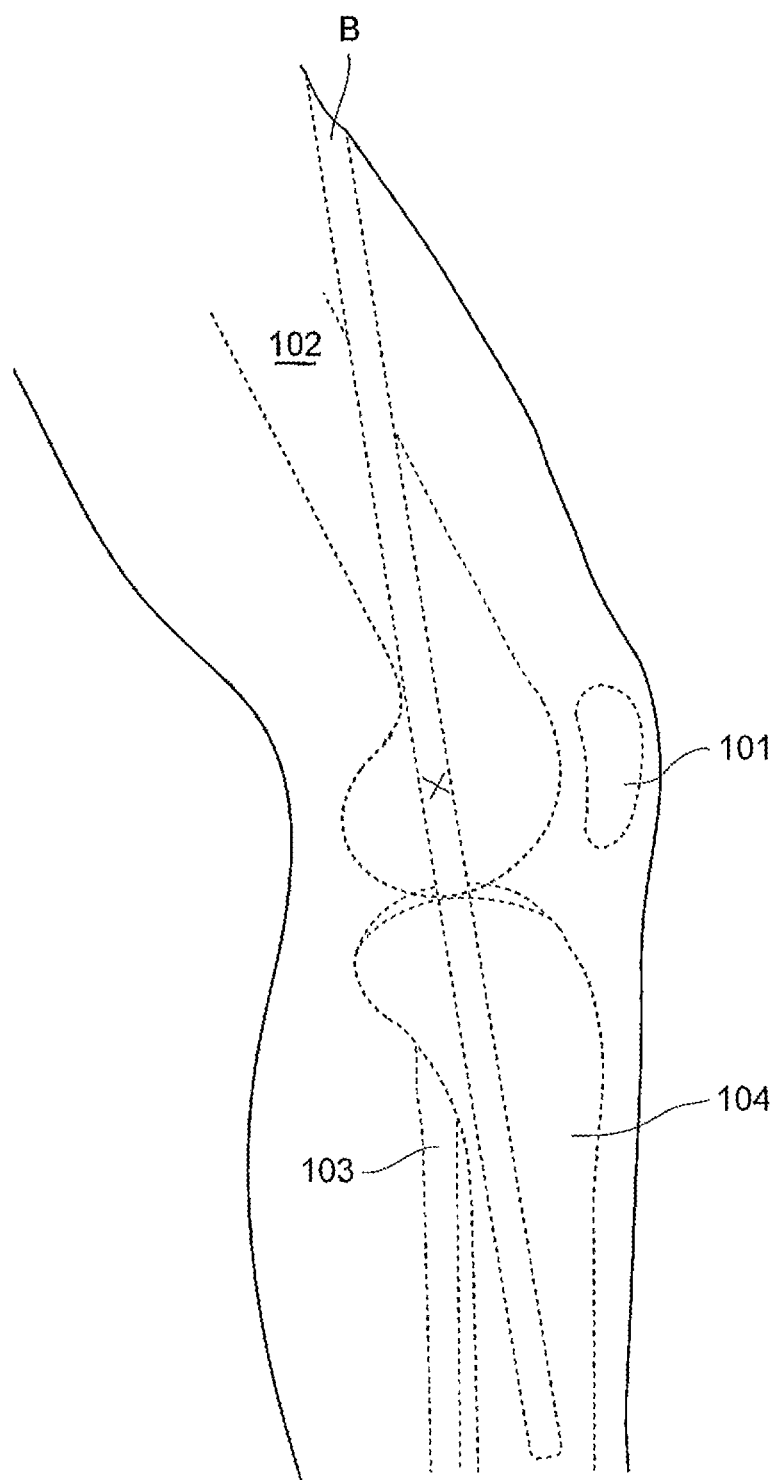
FIG. 2 shows the leg of a patient with dotted lines marking the bones and a bone channel created in the bone.

FIG. 2 shows the left leg of a patient with dotted lines indicating the bone elements of the left leg, the femoral bone 102, the tibial bone 104, the fibula bone 103 and the patella. A bone channel B have been drilled in the bones from a frontal area of the thigh, into the femoral bone 102, penetrating the first cortical bone, entering the cancellous bone of the femoral bone 102 reaching inside of the femoral bone, substantially in the prolongation thereof, penetrating the cortical bone of the distal end of the femoral bone 102 preferably in an area between the lateral and medial condyles, penetrating the cortical bone of the proximal portion of the tibial bone and entering the cancellous bone of the tibial bone 104 substantially in the prolongation thereof.

Figure 3A:
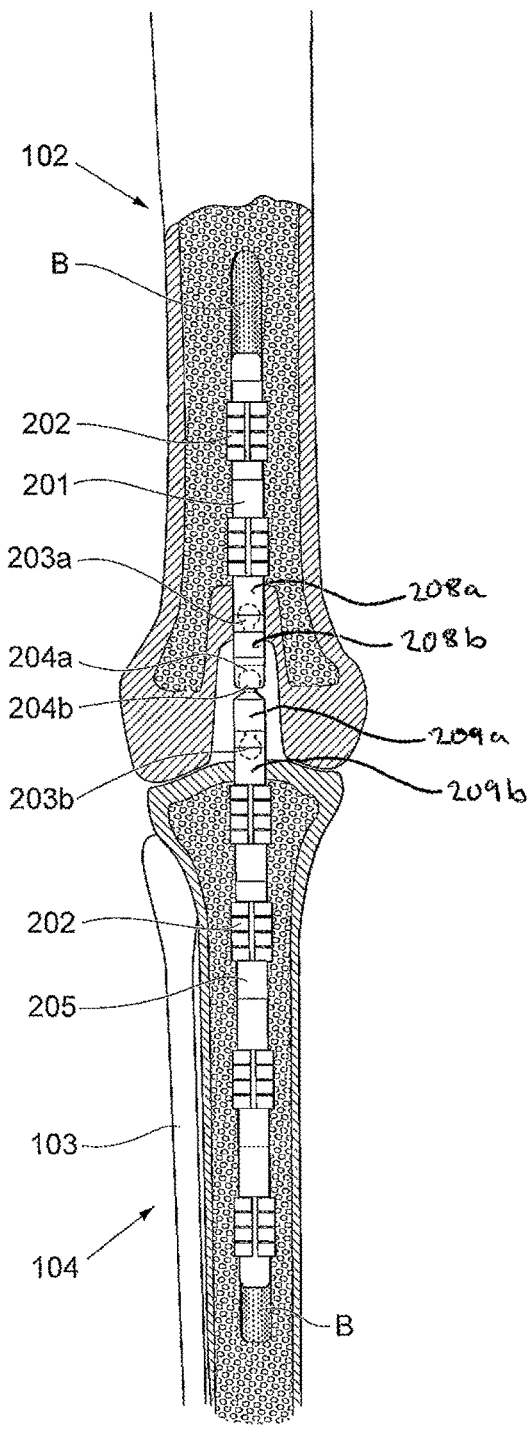
FIG. 3*a* shows a posterior view of a leg of a patient in section.

FIG. 3a shows an anterior view of the leg of the human patient when a bone channel B has been made in the bone, for example as described with reference to FIG. 2. A femoral anchoring device 201 have been introduced through the cortical femoral bone 102 into the cancellous bone of the marrow of the femoral bone 102 at an area proximal to the knee joint, such as an area in the mid-portion of the femoral bone 102. The femoral bone anchoring device 201 have exited the bone marrow through the cortical bone, exiting at an area inside the normal knee joint, here shown as an area between the lateral and medial condyle. The femoral anchoring device shown in FIG. 3a comprises an artificial free joint surface 204a creating at least a part of an artificial knee joint. However, in other embodiments, the femoral anchoring device 201 could be used as a support for at least one artificial knee joint surface, or as a support for at least one artificial knee joint cruciate ligament.

In the embodiment shown in FIG. 3a a tibial anchoring device 205 have further been introduced through the cortical tibial bone 104 into the cancellous bone of the marrow of the tibial bone 104 at an area distal to the knee joint, such as an area in the mid-portion of the tibial bone 104. The tibial bone anchoring device 205 have exited the bone marrow through the cortical bone exiting at an area inside the normal knee joint, here shown as an area centrally of the tibial plateau. The tibial anchoring device shown in FIG. 3a comprises an artificial knee joint surface 204b creating at least a part of an artificial knee joint. However, in other embodiments, the tibial anchoring device 201 could be used as a support for at least one artificial knee joint surface, or as a support for at least one artificial knee joint cruciate ligament, According to the embodiment shown in FIG. 3a, the femoral bone anchoring device 201 and the tibial bone anchoring device 205 are adapted to be movably connected to each other for forming an artificial knee joint by means of the femoral anchoring device comprising an artificial knee joint surface 204a and the tibial bone anchoring device comprising an artificial knee joint surface 204b. The artificial knee joint placed centrally in the natural knee joint assists or replaces the natural knee joint such that the knee joint could be relieved by the artificial joint if weakened, or replaced by the artificial knee joint if the natural knee joint is worn. The femoral 201 and tibial 205 anchoring members provide a stable anchoring of the artificial knee joint which if needed may additionally be supported by an adhesive such as bone cement.

According to one embodiment (not shown) one of the tibial 205 and femoral 201 anchoring devices are adapted only to be fixated to a first cortical bone of the area of the knee joint, the surface of which facing a central position of the knee joint. This embodiment could be conceivable for example in embodiments where the entire bone anchoring device is entering the femoral or tibial bone though a single hole, i.e. the femoral anchoring device and the tibial anchoring device being pre-mounted to each other including the artificial knee joint 204a/204b placed between the femoral anchoring device 201 and tibial anchoring device 205.

In alternative embodiments, the artificial knee joint placed between the femoral anchoring device 201 and the tibial anchoring device 205 is a separate member movably connected to the tibial anchoring device 205 and the femoral bone anchoring device 201.

The femoral anchoring device 201 according to the embodiment shown in FIG. 3a further comprises second joints 203a, 203b allowing movement between a first 208a, 209a and second 208b, 209b portion of the femoral and tibial bone anchoring device, respectively.

Figure 3B:
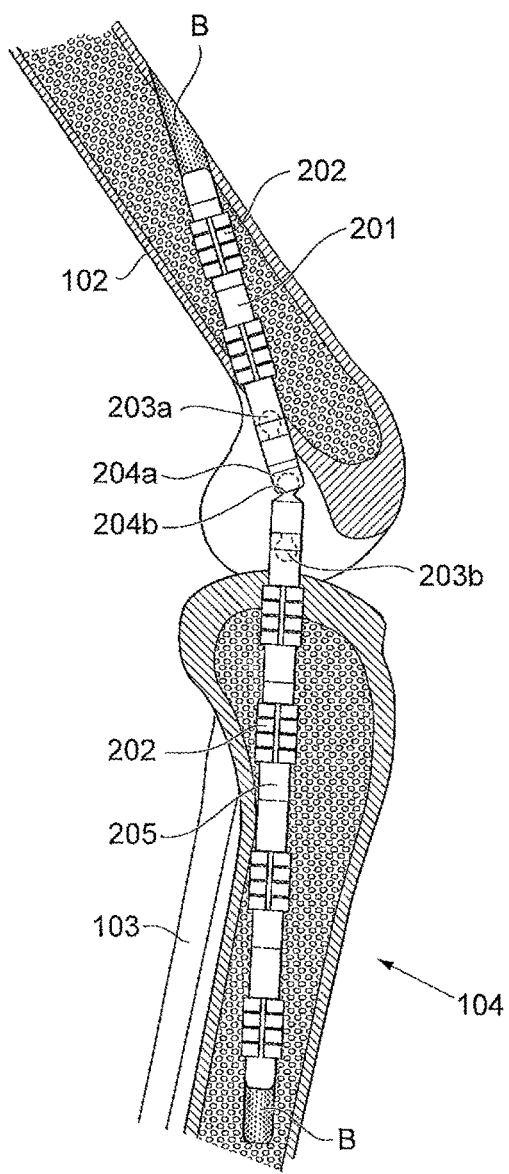
FIG. 3*b* shows a side view of a leg of a patent in section.

FIG. 3b shows the leg of a patient in section, when a medical device comprising a femoral anchoring device 201 and a tibial anchoring device 205 have been placed in a bone channel B. According to the embodiment shown in FIG. 3b the bone channel have been created from one direction and the channel crating member have entered the cortical bone of the femoral bone 102 in one position only and thus creating the channel B as further disclosed with reference to FIG. 2.

The medical device comprising the femoral bone anchoring device 201 and tibial bone anchoring device have been placed in the channel B through the entry hole in the cortical bone of the femoral bone. The medical device is either pre-mounted, such that the femoral anchoring device and the tibial anchoring device is pre-mounted to each o to each prior to the introduction of the medical device into the hole in the femoral bone 102. According to the embodiment shown in FIG. 3b the femoral anchoring device 201 and the tibial anchoring device 205 are movably connected to each other for forming an artificial knee joint by means of the femoral bone anchoring device 201 comprising an artificial knee joint surface 204a and the tibial bone anchoring device 205 comprising an artificial knee joint surface 204b. The artificial knee joint placed centrally in the natural knee joint assists or replaces the natural knee joint such that the knee joint could be relieved by the artificial knee joint if weakened, or replaced by the artificial knee joint if the natural knee joint is worn. The femoral 201 and tibial 205 bone anchoring devices provide a stable anchoring of the artificial knee joint which if needed may additionally be supported by an adhesive such as bone cement.

In FIGS. 3a and 3b the femoral 201 and tibial 205 bone anchoring devices are fixated to the inside of the femoral and tibial bones respectively by radius adjustment devices 202 or expanding members 202 adapted to adjust the maximum radius substantially transverse or at least clearly angled in relation to a center axis of the bone anchoring device, for fixating the femoral 201 and tibial 205 bone anchoring device towards the cortical bone, from the inside of the bone along the elongated portions. The details of the radius adjustment devices are described in further detail with reference to FIGS. 16a-19b.

Figure 5A:
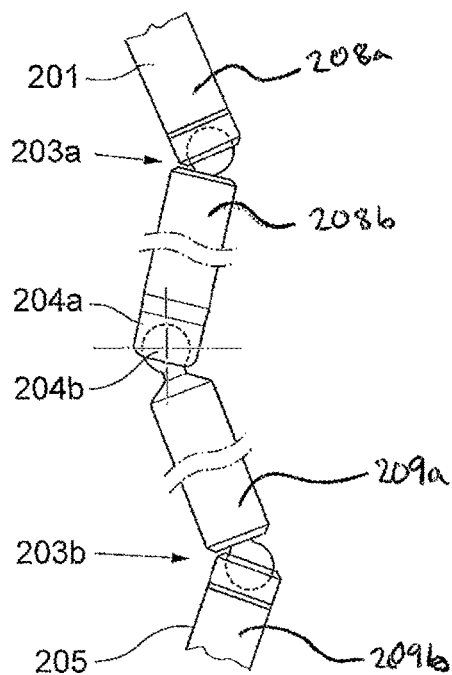
FIG. 5*a* shows an embodiment of the medical device in further detail.
Figure 5B:
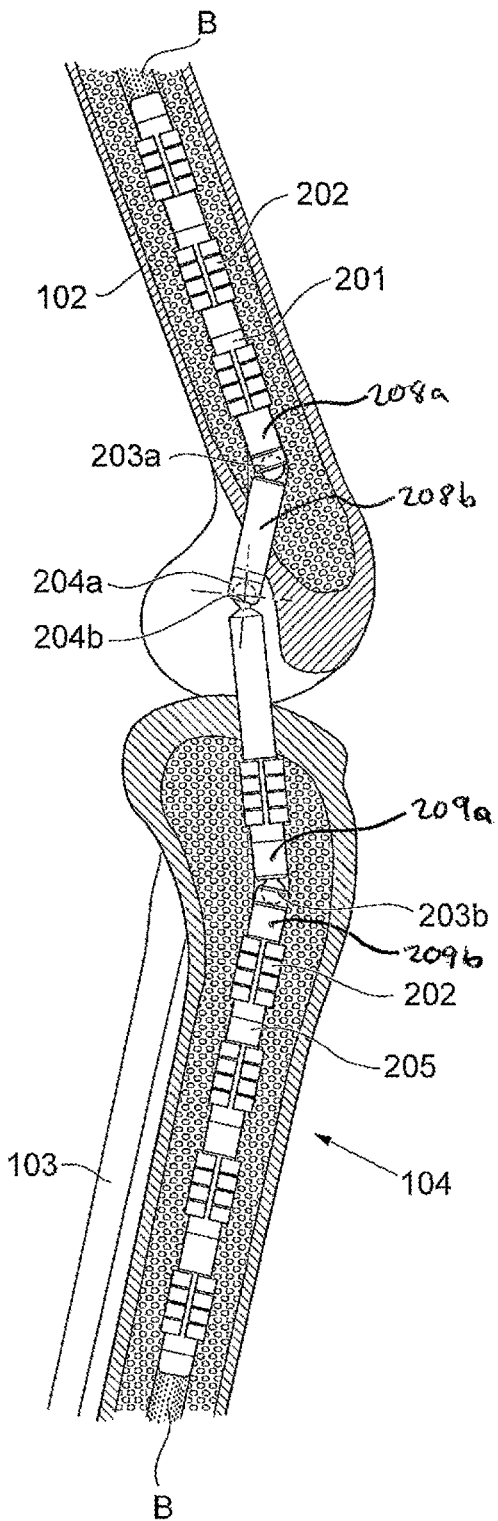
FIG. 5*b* shows a side view of a leg of a patent in section when a medical device according to one embodiment has been implanted.

FIGS. 4a and 4b shows the anchoring devices 201, 205 in an embodiment similar to the previously described with reference to FIGS. 3a and 3b with the difference that in 4a, 4b, the bone channels B have been created both from above, entering the femoral bone 102, and from below, entering the tibial bone 104, which enables the introduction of the tibial bone anchoring device 205 through the hole in the tibial bone 104 and the introduction of the femoral bone anchoring device 201 through the hole in the tibial bone 104, in which case the femoral bone anchoring device 201 having an artificial femoral joint surface and the tibial bone anchoring device 205 having an artificial tibial joint surface meet centrally in the natural knee joint for either connecting to an additional part for forming the artificial joint, or by simply connecting to each other for forming the artificial knee joint FIGS. 5a and 5b shows the second joints 203a, 203b in further detail. The second joint 203a,b allows movement between a first 208a, 209a and second 208b, 209b portion of the femoral and tibial bone anchoring device, respectively. The second joint could enable the precise adjustment of the position of the artificial knee joint comprised of surfaces 204a,b of the femoral bone anchoring device 201 and the tibial bone anchoring device 201. The adjustment could be of great importance since the center of rotation needs to be in the right location for the movement of the artificial knee joint to correspond with the natural movements of the natural hip joint. The second joints could be manually adjustable for example by means of a tool reaching the device through the bone channel B, or using electrical means such as a motor or a solenoid built into the femoral and/or tibial bone anchoring device respectively. The electrical means could be operated using an implantable battery which could communicate via a control unit with a remote or wired control to the outside of the patient. In alternative embodiments the electrical means are operated by means of direct operation in the form of wireless energy, such as magnetic force or induction affecting the electric means being part of the femoral 201 and/or tibial 205 anchoring devices respectively.

Figure 6:
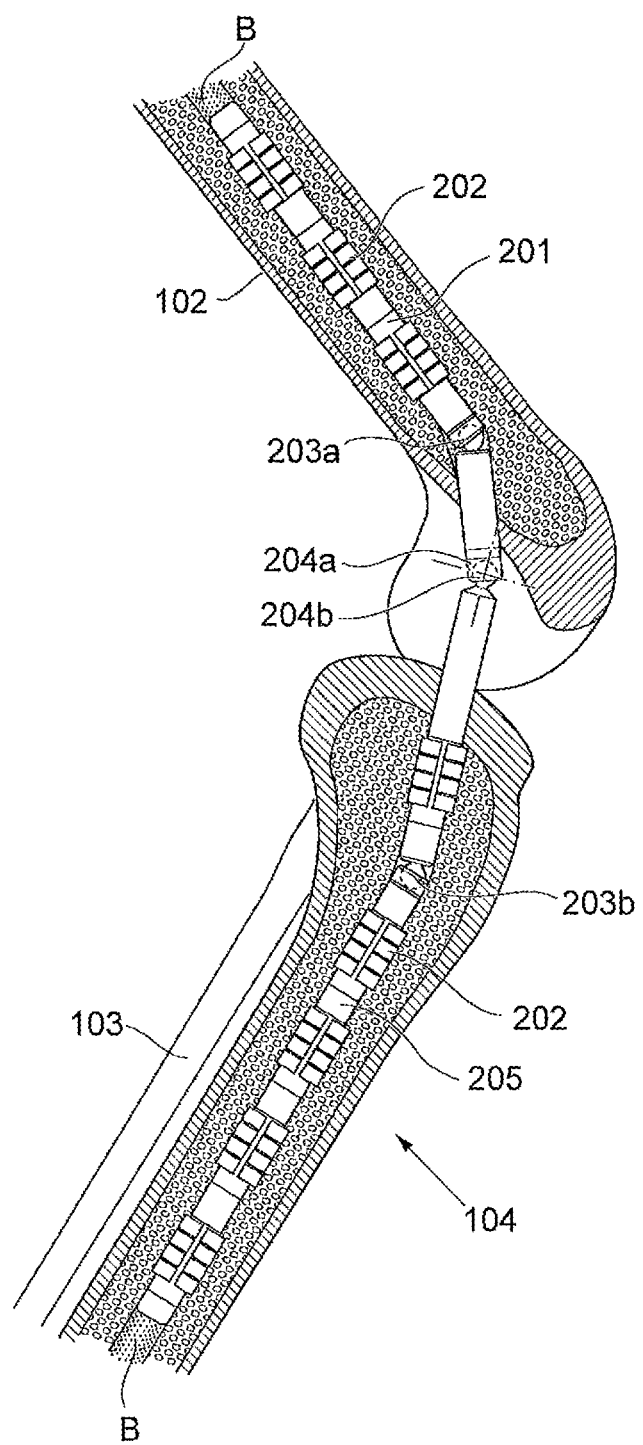
FIG. 6 shows a side view of a leg of a patent in section when a medical device according to one embodiment has been implanted.

FIG. 6 shows the medical device in an embodiment similar to the embodiment shown with reference to FIG. 5b when the second joints 203a, 203b have been used to position the artificial knee joint comprised of the joint surfaces of 204a, 204b of the femoral bone anchoring device 201 and the tibial bone anchoring device 205.

FIG. 7a shows the a posterior view of a leg of a human patient when medical device for creating an artificial knee joint has been implanted. The medical device comprises a transversal member 221 adapted to be placed through four layers of cortical bone 111a, 111b, 111c and 111d of the distal portion of the femoral bone 102, out of the totally four cortical layers along the prolongation of the transversal member 221. The transversal member 221 is adapted to be involved in the artificial knee joint placed centrally between the lateral and medial condyle. The transversal member 221 comprises at least one fixation portion adapted to be involved in fixation of the transversal member 221 to at least one of the four layers of femoral cortical bone 111a-d. In the embodiment shown in FIG. 7a one end of the transversal member 221 comprises a fixed stop 226, whereas the other end of the transversal member 221 comprises a threaded portion to which a nut 225 is attached for fixating the transversal member in the hole though the four layers of cortical bone 111a-d.

According to the embodiment shown in FIG. 7a the transversal member 221 is adapted to be involved in the artificial joint positioned between the lateral and medial condyle and positioned between the normal lateral and medial joint surfaces cranial to the natural joint surfaces of the knee joint.

According to the embodiment shown in FIG. 7a the transversal member 221 comprises the center of rotation and is partially encircled by a portion of a tibial anchoring member 205 having a U-shaped portion 222 adapted to articulate with the transversal member for creating the artificial knee joint.

In other embodiments (not shown) the transversal member 221 is adapted to comprise an artificial knee joint holding part adapted to be involved in holding the artificial knee joint, in which case the artificial knee joint comprises of additional pats.

FIG. 7b shows the tibial bone anchoring device 205 in further detail comprising the U-shaped portion 222 adapted to articulate with the transversal member 221 for crating the artificial knee joint. The tibial bone anchoring device 205 comprises radius adjusting members 202 or expanding members 202 adapted to adjust the maximum radius substantially transverse or at least clearly angled in relation to a center axis of the tibial bone anchoring device 205, for fixating the tibial bone anchoring device 205 towards the cortical bone, from the inside of the bone along the elongated portions. According to the embodiment shown in FIG. 7b, the radius adjustment members 202 are operated by electrical means such as a motor or a solenoid built into the tibial bone anchoring device 205. The electrical means could be operated using an implantable battery which could communicate via a control unit with a remote control 212 on the outside of the patient. In alternative embodiments the electrical means are operated by means of direct operation in the form of wireless energy, such as magnetic force or induction affecting the electric means being part of the tibial 205 anchoring device. The details of the radius adjustment devices are described in further detail with reference to FIGS. 16a-19b.

FIG. 8a shows an embodiment similar to the embodiment described with reference to FIG. 7a, with the difference that the transversal member 221 is adapted to be placed through three layers of cortical bone 111a-c of the distal portion of the femoral bone 102 and be fixated to a fourth layer 111d by means of a threaded portion 227a adapted for fixation in bone.

The tibial anchoring member 205 shown in FIG. 8b is identical to the tibial anchoring member of FIG. 7b, and thus have a construction that is independent of the fixation of the transversal member.

FIG. 9a shows an embodiment similar to the embodiment described with reference to FIG. 7a, with the difference that the transversal member 221 is adapted to be placed through two layers of cortical bone 111a-b of the distal portion of the femoral bone 102 and be fixated to a third layer 111c by means of a threaded portion 227a adapted for fixation in bone.

The tibial anchoring member 205 shown in FIG. 9b is identical to the tibial anchoring member of FIG. 7b, and thus have a construction that is independent of the fixation of the transversal member.

FIG. 10a shows an embodiment of the medical device similar to the embodiment shown with reference to FIGS. 7a, 8a and 9a, with the difference that the medical device further comprises a femoral bone anchoring device 201 for further stabilizing the artificial knee joint comprised of the transversal member 221 and the tibial bone anchoring device 205. The femoral bone anchoring device 201 is similar to the femoral bone anchoring devices described with reference to FIGS. 3a-6, with the difference that the most distal portion 222a of the tibial bone anchoring device 205 is U-shaped and adapted to articulate with around a center of rotation located at the transversal member 221. The U-shaped proximal portion 222a of the tibial bone anchoring device is adapted to interact with the U-shaped portion of the distal portion of the femoral bone anchoring device 201 and in some embodiments the proximal portion 222a of the tibial bone anchoring member and the distal portion 222b of the femoral anchoring member could comprise articulating surfaces such that the proximal portion 222a of the tibial bone anchoring member 205 and the distal portion 222b of the femoral anchoring member 201 could contact each other and articulate and function as joint surfaced of the knee joint supporting the surfaces of the proximal portion 222a of the tibial bone anchoring member 205 and the distal portion 222b of the femoral bone anchoring member 201 articulating with the transversal member 221. The artificial knee joint may of course comprise many different technical solutions and the herein supplied constructions is only examples.

FIG. 10b shows the embodiment of the medical device described with reference to FIG. 10 in a medial view further showing the leg of the patient in section. In the embodiment shown in FIG. 10b, the center of rotation is positioned in the area of the transversal member 221 such that rotating around the transversal member 221 corresponds to the movement of the natural knee joint.

Figure 11:
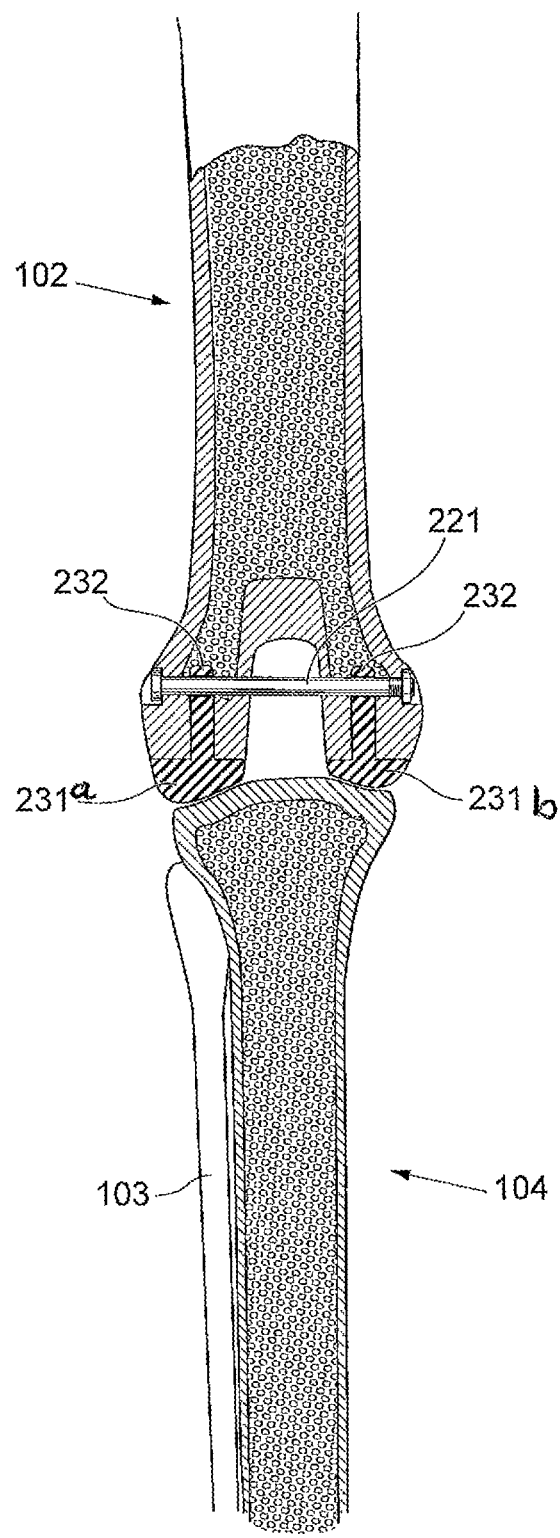
FIG. 11 shows a posterior view of a leg of a patient in section, when artificial joint surfaces have been implanted.

FIG. 11 shows an embodiment in which the transversal member 221 is fixated through four layers of cortical bone (as further disclosed with reference to FIG. 7a). In the embodiment shown in FIG. 11 the transversal member 221 is used to fixate artificial knee joint surfaces 231a,b adapted to at least partially replace the natural knee joint surfaces. The artificial knee joint surfaces 231a,b are adapted to be fixated by means of fixating portions 232 that enters the cancellous bone of the femoral bone and such that the transversal member 221 can penetrate a first layer of cortical bone, a fixating portion 232 of a first artificial knee joint surface 231a, a second layer of cortical bone, exiting into the area between the lateral and medial condyles, entering and penetrating a third layer of cortical bone, penetrating a fixating portion 232 of a second artificial knee joint surface 231b and penetrating a fourth layer of cortical bone for providing a stabile fixation of the artificial knee joint surfaces 231a,b. In the embodiment shown in FIG. 11 one end of the transversal member 221 comprises a fixed stop, whereas the other end of the transversal member 221 comprises a threaded portion to which a nut is attached for fixating the transversal member in the hole though the four layers of cortical bone, however it is equally conceivable that the transversal member 221 is adapted to be placed through three layers of cortical bone of the distal portion of the femoral bone 102 and be fixated to a fourth layer by means of a threaded portion adapted for fixation in bone, as is further described with reference to FIG. 8a. The transversal member provides a very stabile fixation of the artificial knee joint surfaces 231a, 231b, however, if additional fixation is required an adhesive such as bone cement could be used to provide additional fixation. The transversal member 221 may be used to fixate the artificial knee joint surface both at the medial condyle 231b separate or lateral condyle 231a separate. The transversal member may in this case only be fixated to the two cortical bones on each side of the lateral or medial condyle, although this embodiment is not the preferred choice. Furthermore the transversal member may be used to fixate an artificial patella knee surface in the area between the medial and lateral condyle as well (not shown).

FIG. 12a shows the medical device according to an embodiment in which a portion of the femoral and/or tibial bone anchoring device comprises a material or part of material having variable elasticity. In the embodiments shown in FIG. 12a the portion 242 of the of the femoral bone anchoring device 201 comprising material or part of material having variable elasticity have a core portion 242 being less elastic that the surface portion 244, whereas the portion 241 of the tibial bone anchoring device 205 comprising material or part of material having variable elasticity comprises a plurality of portions having variable elasticity. The loosening or anchoring members in bone could be induced by an abnormal strain being placed on the hip joint from e.g. the patient falling or making a rapid movement of the hip. Most anchoring devices are made from a material harder than the bone in which they are anchored, which adds to the tension created between the anchoring devices and the bone of the patient. The portion 241 comprises several sections, schematically denoted I-VII. According to this embodiment the portion 241 is made of a metallic material, which is hardened so that the different sections have different properties. The hardening process can be performed in a way so that there are clear sections with different properties, however it is also conceivable that said different properties propagates the portion 241/242 continuously i.e. there are no clear boarders, rather continuously varying properties throughout the portion 241/242. According to other embodiments the material is a polymer material hardened or stretched to create different properties in the different sections of the hip joint prosthesis. According to other embodiments the hip joint prosthesis is made of ceramic or powder based material, in which case the hip joint prosthesis can be hardened or sintered to produce different properties in the different sections extending along a length axis of the portion 241/242. The proximal section III-V are preferably more elastic for allowing the artificial knee joint fixated to the tibial bone anchoring device 205 to move slightly in relation to the fixating portions comprising the radius adjusting members 222 placed more distal in the tibial bone 104. The distal portions I-II of the portion 241 is preferably less elastic for interacting with the less elastic material of the distal portion of the tibial bone anchoring device 205. This varying elasticity may play an important role as a tool for chock absorbing forces towards the bone. The construction may be done in many different ways to achieve the same goal. Preferable this construction will be combined with the radius adjustment devices disclosed in for example in FIGS. 3a and 3b showing the femoral 201 and tibial 205 bone anchoring devices fixated to the inside of the femoral and tibial bones respectively by the radius adjustment devices 202 or expanding members 202 towards the cortical bone, from the inside of the bone along different portions of the bone adjustment devices. The details of the radius adjustment devices or expanding members are also described in further detail with reference to FIGS. 16a-19b. These radius adjustment devices or expanding members are preferable using the technology of varying elasticity. Similar result as with the varying elasticity could also be achieved by any kind of suspension including spring suspension and the construction may also be bendable or flexible achieving the same result, see FIG. 16a-19b.

FIG. 12b shows the medical device comprising portions 241/242 having varying elasticity in a side view. The varying elasticity could be very advantageous for absorbing large strains induced for example by the patient falling. The portions 241/242 with varying elasticity could be used in any one of the embodiments disclosed herein.

FIG. 13a, 13b shows an embodiment of the medical device similar to the embodiment previously described with reference to FIGS. 3a, 3b, in a posterior and medial view, respectively. The difference being that the distal portion 251 of the femoral bone anchoring device 201 comprises an artificial cruciate ligament holding part 251 adapted to hold an artificial cruciate ligament 253, which in turn is adapted to stabilize the knee joint. Furthermore the proximal portion 252 of the tibial bone anchoring device 205 comprises an artificial cruciate ligament holding part 252 and the artificial cruciate ligament 253 is thus kept in place by the cruciate ligament holding part 251 of the distal portion of the femoral bone anchoring device 201 and the proximal portion 252 of the tibial bone anchoring device 205. By using the femoral and tibial anchoring devices 201, 205 for holding the artificial cruciate ligament 253 the artificial cruciate ligament is kept in place by stable anchoring devices. The bone anchoring devices 201, 205 could be adapted to hole an anterior artificial cruciate ligament or a posterior artificial cruciate ligament, or the bone anchoring devices 201, 205 could be adapted such that both the anterior and posterior artificial cruciate ligament could be fixated to the anchoring devices 201, 205. Preferable mounted on different positions especially in anterior posterior direction.

Figure 14:
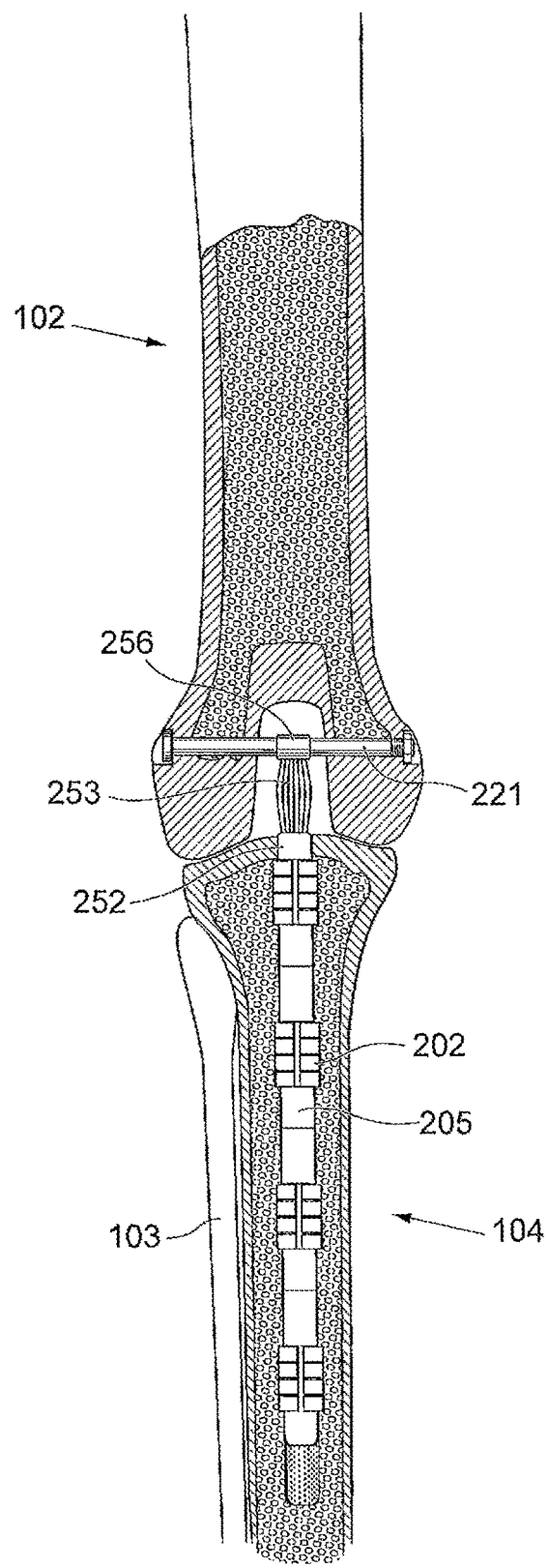
FIG. 14 shows a posterior view of a leg of a patient in section, when an artificial cruciate ligament has been implanted.

FIG. 14 shows an embodiment in which the transversal member 221 (as previously disclosed with reference to FIGS. 7a, 8a, 9a, 10a, 11 and 12a) are adapted to fixate an artificial cruciate ligament 253, which could be an anterior artificial cruciate ligament or a posterior artificial cruciate ligament, or both the anterior and posterior artificial cruciate ligament. Preferable mounted on different positions both in anterior posterior direction and medial lateral direction. The support part 256 may be extended in different directions. The transversal member provides a stable fixation member for the artificial cruciate ligament 253, which in the other end is fixated to a tibial bone anchoring device 205. In alternative embodiments the cruciate ligament is the natural cruciate ligament and the transversal member 221 only supports the movement of the natural cruciate ligament. In yet other alternatives the cruciate ligament is a portion of the patella tensor used to create a "natural" artificial cruciate ligament.

Figure 15:
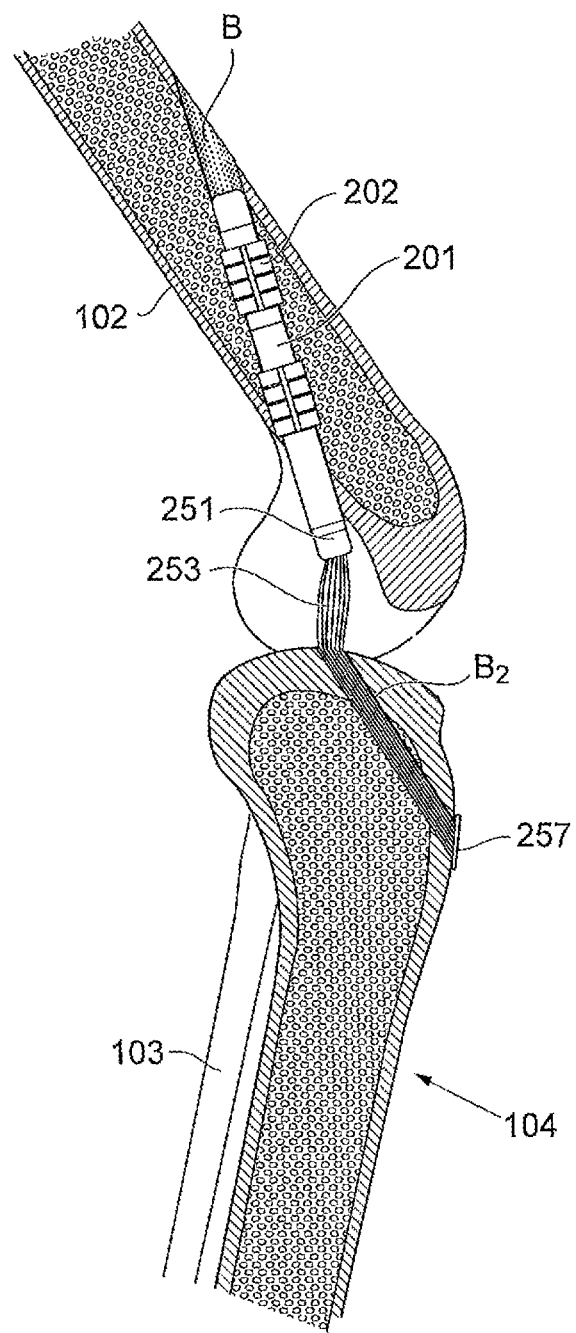
FIG. 15 shows a side view of a leg of a patient in section, when an artificial cruciate ligament has been implanted.

FIG. 15 shows an embodiment in which the artificial cruciate ligament at the proximal end is fixated to a femoral bone anchoring device 201 comprising a cruciate ligament holding part 251, and the distal end of the artificial cruciate ligament is fixated to in or through a bone channel B2. In the embodiment shown in FIG. 15 the cruciate ligament 253 is fixated by means of a fixation button, such that the cruciate ligament 253 is hindered from moving back into the bone channel B2.

Figure 16A:
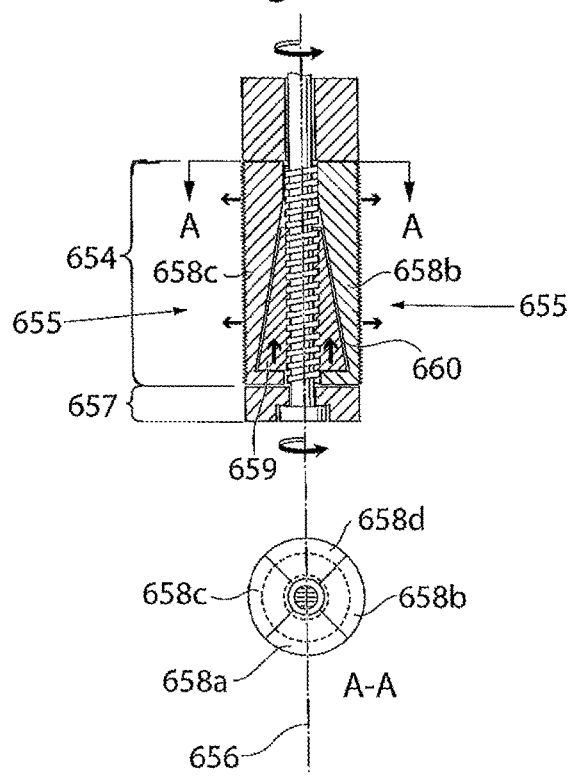
FIG. 16a shows a radius adjustment member according to one embodiment in further detail, in a first state.

FIG. 16a shows a radius adjustment member for fixating the bone anchoring members (201, 205 throughout the application) to the inside of the cortical bone of the patient. The a radius adjustment member comprising an expanding portion 654, and a bone contacting surface 655 on the expanding portion 654. The expanding portion 654 is adapted to be at least partially inserted into the bone of a patient and to expand within the bone such that the bone contacting surface 655 is placed in contact with the inside of the bone for fixating the bone anchoring device to the inside of the bone. The radius adjustment member has a centrally placed longitudinal axis and the expanding portion 654 comprises a plurality of expansion members 658a-d, adapted to expand radially away from the longitudinal axis 656. One advantage with using the radius adjustment member is that bone cement, normally used for fixation purposes, could create a bodily macrophage reaction excavating the bone cement and thus causing loosening of the fixation. Other fixations, such as fixations using orthopedic screws penetrating the bone could also create a bodily reaction rejecting the foreign matter of the medical device. Eliminating the use of bone cement and orthopedic screws, and at the same time creating a stabile fixation would be very advantageous, furthermore, creating a fixation that has the ability to move slightly in the fixation in response to exposure to force e.g. from the patient falling would be even more advantageous.

Figure 16B:
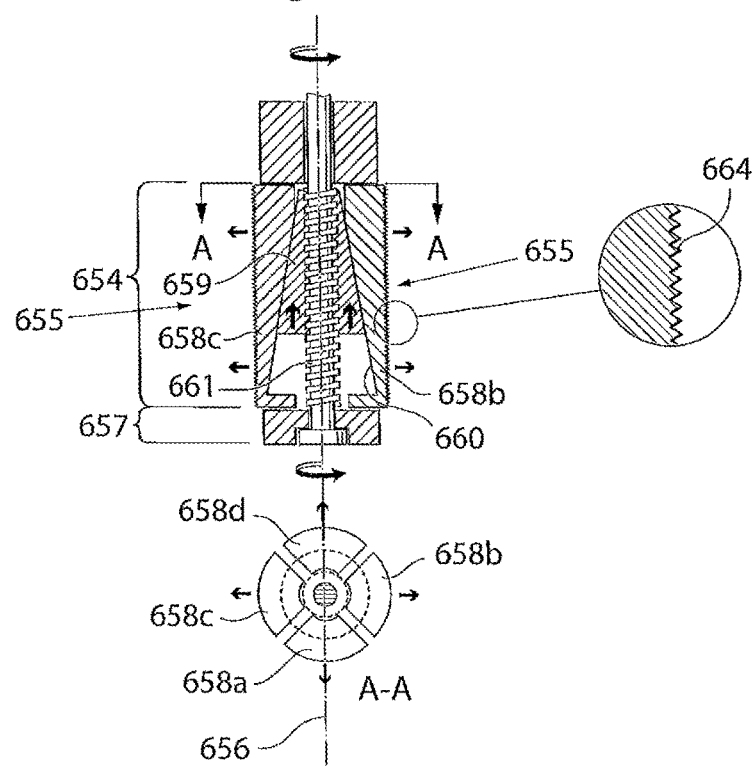
FIG. 16b shows a radius adjustment member according to one embodiment in further detail, in a second state.

The radius adjustment member according to the embodiment shown in FIG. 16a/16b further comprises an operating device 659 adapted to operate the expanding portion 564, according to the embodiment shown in FIG. 16a, 16b the operating device 659 comprises a conical member 659 adapted to contact a corresponding surface 660 of the expanding portion 654 for expanding the expanding portion 654. The operating device 659 further comprises a rotatable threaded portion 661 adapted to engage a corresponding threaded portion of the conical member 659 for moving the conical member 659 along the centrally placed longitudinal axis 656 in the direction of the connecting portion 653. The threaded portion 661 is a portion of an elongated member 662, which according to the embodiment shown in FIG. 3a, 3b reaches from the end portion 657 to the top part of the prosthetic contacting portion 45 having a tool engaging portion 663, such that the elongated member 662 can be rotated using a tool for rotating the threaded portion and thereby the moving the conical member 659. According to other embodiments, the operating device could be operated using electrical means such as a motor or a solenoid built into the bone anchoring device. The electrical means could be operated using an implantable battery which could communicate via a control unit with a remote or wired control to the outside of the patient. In alternative embodiments the electrical means are operated by means of direct operation in the form of wireless energy, such as magnetic force or induction affecting the electric means.

The bone contacting surfaces 655, according to the embodiments shown in FIG. 16a, 16b comprise needle or nail like tapered members 664 adapted to at least partially enter the bone of the inside thereof for further fixating the bone anchoring device in the bone, especially axially along the centrally placed longitudinal axis 656. In other embodiments, not shown, the bone contacting surface comprises a porous micro- or nano-structure adapted to promote the in-growth of bone in the medical device. The bone contacting surface 655 is here described in relation to the embodiment of FIGS. 16a and 16b, however the adaptation of the bone contacting surface 655 is equally applicable in all of the embodiments disclosed herein.

FIG. 16b shows the radius adjustment member according to the embodiment shown in FIG. 16a when the elongated member 662 has been rotated by means of a tool or electrical means such that the threaded portion 661 has moved the conical member 659 affecting the corresponding surface of the expansion members 658 a-d and thus expanding the expanding portion 654 such that the bone contacting surface 655 is adapted to be placed in contact with the inside of the femoral bone.

Figure 17A:
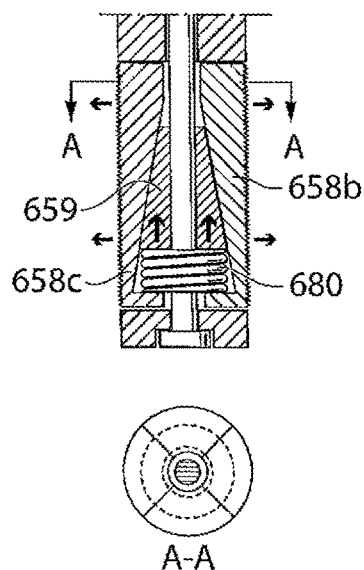
FIG. 17a shows a radius adjustment member according to one embodiment in further detail, in a first state.
Figure 17B:
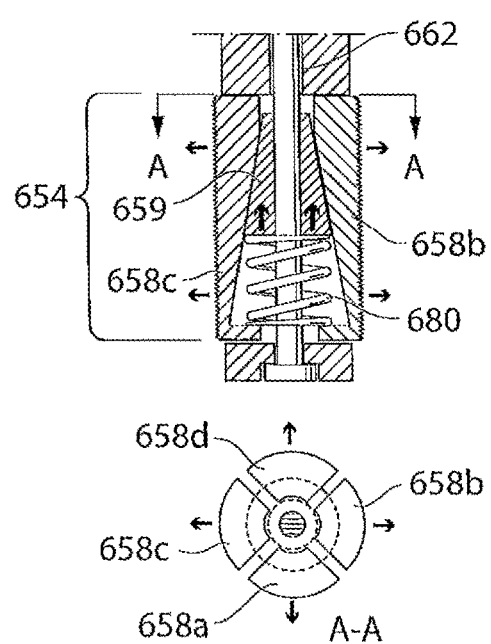
FIG. 17b shows a radius adjustment member according to one embodiment in further detail, in a second state.

FIGS. 17a and 17b shows the medical device in an embodiment similar to the embodiment disclosed with reference to FIGS. 16a and 16b, however in the embodiment of FIGS. 17a and 17b the operation device of the medical device further comprises an elastic operation device 680 adapted to press on the conical member 659 for expanding the expanding portion 654. The elastic member could be adapted to be released after the insertion of the radius adjustment member into the bone 5 thereby creating an elastic pressure on the expansion members 658a, 658b for elastically pressing the bone contacting surfaces 655 onto the inside of the bone. The elastic operation device 680 is according to the embodiment shown in FIGS. 17a and 17b released by turning the elongated member 662 with a tool or electric means engaging the tool engaging portion 663. The elastic portion enables a fixation of the radius adjustment member to the bone that has the ability to move slightly in the fixation in response to exposure to force e.g. from the patient falling. In the embodiment shown in FIGS. 17a and 17b the elastic operation device 680 is a spring which could be a linear spring or a non-linear spring allowing a first movement with a first elasticity and further movement with a second elasticity that requires greater force. The elastic operation device could according to other embodiments comprise an elastic material, such as an elastomer.

FIG. 17b shows the medical device when the elastic operation device 680 has been released such that the expanding portion has been expanded pressing the bone contacting surfaces against the inside of the bone.

Figure 18A:
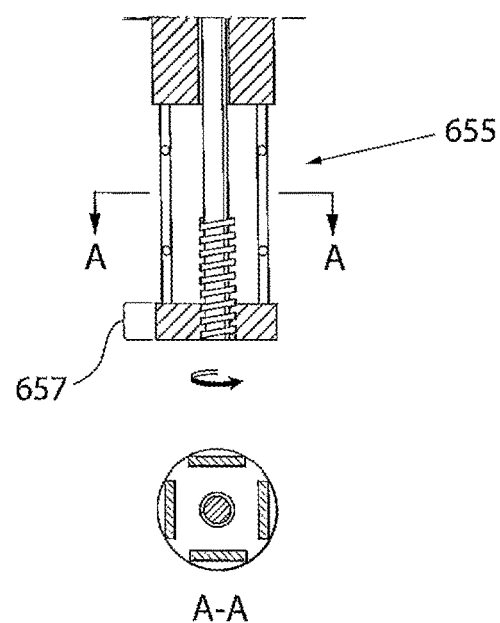
FIG. 18a shows a radius adjustment member according to one embodiment in further detail, in a first state.
Figure 18B:
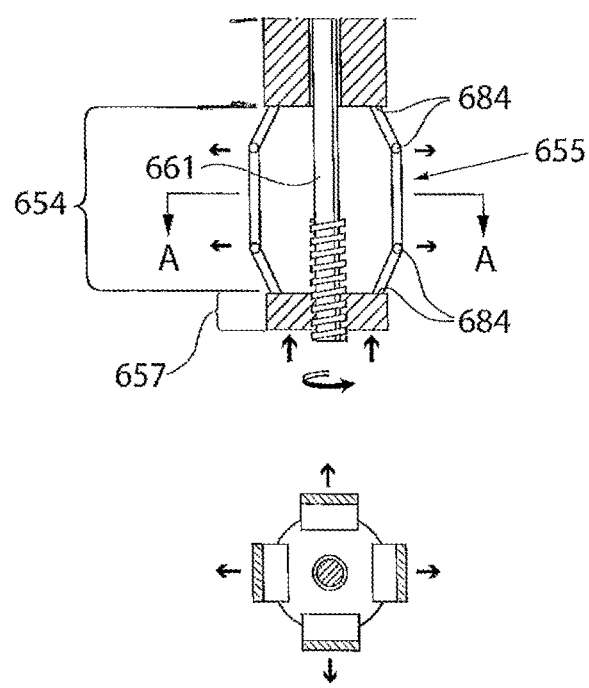
FIG. 18b shows a radius adjustment member according to one embodiment in further detail, in a second state.

FIGS. 18a and 18b shows the radius adjustment member according to an embodiment in which the expanding portion 654 comprises a deformable expanding portion 654, wherein the expanding portion expands by the deformable expanding portion 654 deforming, such that the bone contacting surface 655 is placed in contact with the inside of the femoral bone for fixating the radius adjustment member to the femoral bone. The deformable expanding portion 654 deforms at deformation points 684 by the threaded member 661 pulling the end portion 657 towards the connecting portion 653 thus expanding the expanding portion 654 pushing the bone contacting surfaces 655 radially such that they are placed in contact with the inside of the bone.

FIG. 18b shows the medical device when the deformable expanding portion 654 has expanded pressing the bone contacting surfaces 655 against the inside of the bone.

FIG. 19a shows the radius adjustment member according to an embodiment in which the radius adjustment member has a centrally placed longitudinal axis 656, wherein the radius adjustment member comprises a plurality of expanding portions 654 a-d, distributed axially along the longitudinal axis 656 of the medical device. The plurality of expanding portions 654a-d distributed axially along the longitudinal axis 656 of the radius adjustment member is adapted to radially expand independently of each other, to allow different expansion of the different expanding portions 654 a-d. The different expansion could allow the expanding portions 654 a-d to adapt to the uneven surfaces of the anatomy of the inside of the bone. Since the different expanding portions expand independently of each other, one expanding portion 654a will expand until the bone contacting surface 655 of that particular expanding portion is placed in contact with the bone of the inside of the bone, after which the other expanding portions 654 b-d will continue to expand until their respective bone contacting surface is placed in contact with the inside of the bone. Each expanding portion comprises four expansion members 658 a-d each having a sloped surface 660 corresponding to a sloped surface 696 of the conical members 659, such that the conical members presses the expansion members radially from the longitudinal axis 656 when the conical members 659 are moved in the direction of the connecting portion 653.

FIG. 19b shows the medical device when the expanding portions 654a-d has been expanded for pressing the bone contacting surfaces 655 against the inside of the bone.

Please note that any embodiment or part of embodiment as well as any method or part of method could be combined in any way. All examples herein should be seen as part of the general description and therefore possible to combine in any way in general terms.

The invention claimed is:

1. A medical device for assisting in the fixation of an artificial knee joint or artificial cruciate ligament of a mammal patient comprising a bone anchoring device, comprising at least one of;
   i. a tibial bone anchoring device adapted to be introduced through the cortical tibia bone into the bone marrow of the tibia bone at an area distal to the knee joint and
   ii. a femoral bone anchoring device, adapted to be introduced through the cortical femur bone into the bone marrow of the femur bone at an area proximal to the knee joint,
   wherein the bone anchoring device is further adapted to exit the bone marrow through the cortical bone at an area site inside the natural knee joint, wherein the bone anchoring device comprises at least one of;
   iii. a support for at least one artificial knee joint surface,
   iv. a support for at least one artificial knee joint cruciate ligament and
   v. at least one artificial knee joint surface for creating at least a part of an artificial knee joint;
   wherein a part of the bone anchoring device is configured to be placed in the bone marrow and comprises at least one radius adjustment member comprising a plurality of independently expanding portions, adapted to adjust the maximum radius substantially transverse or at least clearly angled in relation to a center axis of the bone anchoring device, wherein said independently expanding portions are adapted to expand independently of each other, for fixating the bone anchoring device towards the cortical bone, from the inside of the bone, when implanted in the bone marrow of the femur or tibia bone.

2. The medical device according to claim 1, comprising an artificial knee joint surface adapted to be placed at the lateral condyle of the femur.

3. The medical device according to claim 1, comprising an artificial knee joint surface adapted to be placed at the medial condyle of the femur.

4. The medical device according to claim 1, wherein the tibial bone anchoring device is adapted to be connected to a second femoral bone anchoring device and adapted to pass the femoral cortical bone only on a site placed inside the natural knee joint the medical device further comprising at least one artificial knee joint movable connecting the tibial and femoral bone anchoring device.

5. The medical device according to claim 1, wherein the femoral bone anchoring device is adapted to be connected to a second tibial bone anchoring device and adapted to pass the tibial cortical bone only on a site placed inside the natural knee joint the medical device further comprising at least one artificial knee joint movable connecting the tibial and femoral bone anchoring device.

6. The medical device according to claim 1, further comprising at least one artificial knee joint movably connected to the tibial anchoring device and the femoral bone anchoring device.

7. The medical device according to claim 1, wherein the femoral bone anchoring device and the tibial bone anchoring device are adapted to be movably connected to each other for forming an artificial knee joint.

8. The medical device according to claim 1, wherein the tibial bone anchoring device further comprises a second joint allowing movement between a first and second portion of the tibial bone anchoring device.

9. The medical device according to claim 8, wherein the first portion of the tibial bone anchoring device is an anchoring portion, and wherein the second portion of the tibial bone anchoring device is a support portion for at least one of; supporting the artificial knee joint surface, supporting the at least one artificial knee joint cruciate ligament, and comprising at least one artificial knee joint surface.

10. The medical device according to claim 8, wherein the artificial knee joint and the second joint are adapted to be adjustable for adjusting the angle or position of the artificial knee joint support, cruciate ligament support or artificial knee joint surface.

11. The medical device according to claim 1, wherein the femoral bone anchoring device further comprises a second joint allowing movement between a first and second portion of the femoral bone anchoring device.

12. The medical device according to claim 11, wherein the first portion of the femoral bone anchoring device is an anchoring portion, and wherein the second portion of the femoral bone anchoring device is a support portion for supporting at least one of; the at least one artificial knee joint cruciate ligament and the at least one artificial knee joint surface.

13. The medical device according to claim 1, wherein in a natural knee joint, surfaces are placed both at the medial and lateral femoral condyle, wherein the artificial knee joint is adapted to be placed between the natural lateral and medial joint surfaces, when implanted.

14. The medical device according to claim 1, wherein in a natural knee joint, surfaces are placed between the tibial and femoral bones both at the medial and lateral femoral condyle, wherein the artificial knee joint is adapted to be placed more cranial than the natural lateral and medial joint surfaces, when implanted.

15. The medical device according to claim 1, wherein the artificial knee joint is adapted to form one single artificial knee joint with two contacting joint surfaces adapted to replace both the two lateral contacting surfaces and the two medial contacting surfaces existing in natural knee joint, when implanted.

16. The medical device according to claim 1, wherein the part of the bone anchoring device placed in the bone marrow comprises cortical bone contacting surfaces adapted to contact the cortical bone from the inside of the tibia or femur bone, wherein at least one of the conical bone contacting surfaces and the related material in the bone anchoring device have a suspension in relation to the cortical bone, wherein the suspension comprising at least one of, a bendable part and an elastic part of the bone anchoring device for a shock absorbing fixation of the bone anchoring device towards the conical bone when implanted in the bone marrow of the femur or tibia bone.

17. The medical device according to claim 1, wherein the bone anchoring device is adapted to be able to drill in the tibia or femur bone.

18. The medical device according to claim 1, further comprising at least one artificial cruciate ligament adapted to be fixated to the artificial cruciate ligament support with its first end.

19. The medical device according to claim 18, wherein a second cruciate ligament end, placed on the opposite end to the first cruciate ligament end, is adapted to be mounted through a bone channel in the tibial or femoral bone and adapted to be fixated to the bone at at least one of; the inside of the bone channel, and on the outside of the knee joint after passing through the bone channel, when implanted.

20. The medical device according to claim 18, comprising two artificial cruciate ligaments, the anterior and posterior cruciate ligament adapted to be fixated to the artificial cruciate ligament support.

21. The medical device according to claim 1, wherein a knee joint has a femoral joint surface and a tibial joint surface both placed in the position of the medial femoral condyle and the lateral femoral condyle, wherein the bone anchoring device is adapted to support at least one artificial joint surface, being adapted to be positioned in at least one of the position of the lateral and medial femoral condyle and connected to the bone anchoring device.

22. The medical device according to claim 21, comprising at least one artificial joint surface being adapted to be positioned at least in one of the position of the lateral and medial femoral condyle and fixated to the bone anchoring device.

23. The medical device according to claim 1, further comprising a transversal member adapted to be placed through at least three layers of cortical bone of the distal portion of the femoral bone, out of totally four cortical layers along a prolongation of the transversal member, wherein the transversal member is adapted to be involved in the artificial knee joint or the artificial cruciate ligament and wherein the transversal member comprises at least one fixation portion adapted to be involved in fixation of the transversal member to at least one of the at least four layers of femoral cortical bone.

24. The medical device according to claim 23, wherein the transversal member is adapted to be involved in the artificial joint positioned between the lateral and medial condyle.

25. The medical device according to claim 23, wherein the transversal member is adapted to be involved in the artificial joint positioned between the natural lateral and medial joint surfaces.

26. The medical device according to claim 23, wherein the transversal member adapted to be involved in the artificial joint positioned cranial to the natural joint surfaces of the knee joint.

27. The medical device according to claim 23, wherein the transversal member is adapted to comprise the center of rotation of the artificial knee joint.

28. The medical device according to claim 23, wherein the transversal member is adapted to be placed through four layers of cortical bone of the distal portion of the femoral bone.

29. The medical device according to claim 23, wherein the transversal member comprises an artificial knee joint surface adapted to articulate with another artificial knee joint surface fixated to the tibial bone.

30. The medical device according to claim 23, wherein the transversal member comprises an artificial knee joint holding part adapted to be involved in holding the artificial knee joint.

31. The medical device according to claim 23, wherein the transversal member is adapted to be placed through three layers of cortical bone of the distal portion of the femoral bone and be fixated to a fourth layer of cortical bone of the distal portion of the femoral bone.

32. The medical device according to claim 23, wherein the transversal member is adapted to:
   a. be placed through two layers of cortical bone of a first condyle of the distal portion of the femoral bone,
   b. be placed through an artificial knee joint element fixated to the tibial bone, and
   c. be placed through or fixated in at least a third layer of cortical bone of the second condyle of the distal portion of the femoral bone.

33. The medical device according to claim 23, wherein the transversal member is adapted to:
   d. be placed through two layers of cortical bone of a first condyle of the distal portion of the femoral bone,
   e. be placed through an artificial knee joint element fixated to the tibial bone,
   f. be placed through a third layer of cortical bone of the second condyle of the distal portion of the femoral bone, and
   g. be placed through or fixated in a fourth layer of cortical bone of the second condyle of the distal portion of the femoral bone.

34. The medical device according to claim 23, wherein the transversal member is adapted to be connected to a femoral anchoring member in an area between the medial and lateral condyles.

35. The medical device according to claim 23, wherein the transversal member is adapted to be connected to a tibial anchoring member in an area between the medial and lateral condyles.

36. The medical device according to claim 23, wherein the artificial knee joint comprises the connection between the transversal member and the tibial anchoring member.

37. The medical device according to claim 23, wherein the medical device further comprises at least one artificial cruciate ligament adapted to be fixated to the transversal member at a first cruciate ligament end.

38. The medical device according to claim 23, wherein the artificial knee joint is further defined as a natural knee joint being stabilized by and comprising the transversal member adapted to stabilize the cruciate ligaments.

39. The medical device according to claim 23, wherein the transversal member is adapted to connect to an artificial knee joint surface at the medial condyle of the femur.

40. The medical device according to claim 23, wherein the medical device further comprises two artificial cruciate ligaments, one anterior and one posterior cruciate ligament adapted to be fixated to the transversal member on at least one of, the same or different positions on the transversal member.

41. The medical device according to claim 23, wherein the transversal member has an elongated part, elongated in the anterior and posterior direction and adapted to be placed between the medial condyle and the lateral condyle to accommodate the different positions of the cruciate ligaments.

42. The medical device according to claim 23, comprising: a transversal member adapted to be placed through at least three layers of cortical bone of the distal portion of the femoral bone, out of totally four cortical layers in the elongation of the transversal member, wherein the transversal member comprises at least one fixation portion adapted to be involved in fixation of the transversal member to at least one of the at least four layers of femoral cortical bone, and wherein the transversal member is adapted to be involved in at least one of; the artificial knee joint and an artificial cruciate ligament support.

43. The medical device according to claim 1, comprising a transversal member adapted to be placed through at least two layers of femoral cortical bone involving both femoral condyles, wherein the transversal member comprises at least one artificial knee joint or cruciate ligament holding part adapted to be involved in at least partly holding the artificial knee joint or artificial cruciate ligament.

44. The medical device according to claim 43, wherein the transversal member comprises at least one artificial knee joint surface.

45. The medical device according to claim 43, wherein the transversal member is adapted to comprise the center of rotation of the artificial knee joint.

46. The medical device according to claim 43, wherein the transversal member comprises an artificial knee joint surface adapted to articulate with another artificial knee joint surface being part of the bone anchoring device.

* * * * *